US012799199B2

(12) United States Patent
Bisht et al.

(10) Patent No.: US 12,799,199 B2
(45) Date of Patent: Nov. 17, 2026

(54) ANTIBODIES AND METHODS OF USE

(71) Applicant: Oxford BioTherapeutics Ltd, Oxford (GB)

(72) Inventors: Arnima Bisht, San Jose, CA (US); James Edward Ackroyd, Oxford (GB)

(73) Assignee: Oxford BioTherapeutics Ltd, Oxford (GB)

( * ) Notice: Subject to any disclaimer, the term of this patent is extended or adjusted under 35 U.S.C. 154(b) by 1316 days.

(21) Appl. No.: 17/622,499

(22) PCT Filed: Jul. 2, 2020

(86) PCT No.: PCT/GB2020/051588
§ 371 (c)(1),
(2) Date: Dec. 23, 2021

(87) PCT Pub. No.: WO2021/001653
PCT Pub. Date: Jan. 7, 2021

(65) Prior Publication Data

US 2022/0372137 A1 Nov. 24, 2022

Related U.S. Application Data

(60) Provisional application No. 62/965,450, filed on Jan. 24, 2020, provisional application No. 62/870,269, filed on Jul. 3, 2019.

(51) Int. Cl.

*C07K 16/28* (2006.01)
*A61K 39/395* (2006.01)
*A61P 35/00* (2006.01)

(52) U.S. Cl.

CPC .... *C07K 16/2803* (2013.01); *A61K 39/39558* (2013.01); *A61P 35/00* (2018.01); *C07K 2317/24* (2013.01); *C07K 2317/55* (2013.01); *C07K 2317/565* (2013.01); *C07K 2317/567* (2013.01); *C07K 2317/74* (2013.01); *C07K 2317/76* (2013.01); *C07K 2317/77* (2013.01); *C07K 2317/92* (2013.01)

(58) Field of Classification Search

None
See application file for complete search history.

(56) References Cited

U.S. PATENT DOCUMENTS

| | | | | |
|---|---|---|---|---|
| 5,576,423 | A | 11/1996 | Aversa et al. | |
| 2015/0017721 | A1* | 1/2015 | Muller ................. | C12N 5/0646 435/375 |
| 2016/0159905 | A1 | 6/2016 | Abdiche et al. | |

FOREIGN PATENT DOCUMENTS

| | | | |
|---|---|---|---|
| CN | 101627055 | A | 1/2010 |
| CN | 108064166 | A | 5/2018 |
| WO | 2008/027739 | A2 | 3/2008 |
| WO | 2014/100740 | A1 | 6/2014 |
| WO | 2015/104711 | A1 | 7/2015 |
| WO | 2017/004330 | A1 | 1/2017 |

OTHER PUBLICATIONS

Paul, Fundamental Immunology, 3rd Edition, 1993, pp. 292-295 (Year: 1993).*

Bendig M. M. (Methods: A Companion to Methods in Enzymology, 1995; 8:83-93) (Year: 1995).*

Rudikoff et al. (Proceedings of the National Academy of Sciences USA, vol. 79, p. 1979-1983, 1982) (Year: 1982).*

Dubel (Handbook of Therapeutic Antibodies, 2007, p. 100-101) (Year: 2007).*

Bottino, C. et al., "NTB-A [correction of GNTB-A], a novel SH2D1A-associated surface molecule contributing to the inability of natural killer cells to kill Epstein-Barr virus-infected B cells in X-linked lymphoproliferative disease," J Exp Med., vol. 194(3):235-246 (2001).

Chatterjee, M. et al., "CD3-T cell receptor co-stimulation through SLAMF3 and SLAMF6 receptors enhances ROR gamma t recruitment to the IL 17A promoter in human T lymphocytes," J. Biol. Chem., vol. 287:38168-38177(2012).

Eissmann, P. et al., "Molecular analysis of NTB-A signaling: a role for EAT-2 in NTB-A-mediated activation of human NK cells," J. Immunol., vol. 177:3170-3177 (2009).

International Preliminary Report on Patentability, PCT/GB2020/051588, dated Dec. 28, 2021, 7 pages.

International Search Report and Written Opinion, PCT/GB2020/051588, dated Oct. 5, 2020, 10 pages.

* cited by examiner

*Primary Examiner* — Julie Wu

(74) *Attorney, Agent, or Firm* — Nelson Mullins Riley & Scarborough LLP; Jane E. Remillard, Esq.; Jill Gorny Sloper, Esq.

(57) ABSTRACT

The present invention relates to antibodies and other therapeutic proteins directed against SLAM family member 6 (SLAMF6) also known as NTB-A or CD352, nucleic acids encoding such antibodies and therapeutic proteins, methods for preparing antibodies and other therapeutic proteins, and methods for the treatment of diseases, such as cancers, by using antibodies and other therapeutic proteins directed against SLAMF6.

23 Claims, 11 Drawing Sheets

Specification includes a Sequence Listing.

Figure 1a

1B3 VH chain, SEQ ID NO:1

QVQLKQSGAE LVRPGTSVKV SCKASGYAFT NYLIEWVKQR PGQGLEWIGV INPGSGGTNY
NEKFKDKATL TADKSSNTAY MQLSSLTSDD SAVYFCARRG WDYFDYWGQG TTLTVSS

Figure 1b

1B3 VL chain, SEQ ID NO:2

QIVLTQSPAL MSTSPGEKVT MTCSASSSVS YIYWFQQKPG SSPKPWIYRT SNLASGVPAR
FSGSGSGTSY SLTISSMEAE DAATYYCQQW DNNPYTFGGG TKLEIK

Figure 2a

1B3(humanised) VH chain, SEQ ID NO:13

QVQLVQSGAE VKKPGASVKV SCKASGYAFT NYLIEWVRQA PGQGLEWIGV INPGSGGTNY
NEKFQGRVTL TADKSISTAY MELSRLRSDD TAVYYCARRG WDYFDYWGQG TLVTVSS

Figure 2b

1B3(humanised) VL chain, SEQ ID NO:14

DIQLTQSPSS LSASVGDRVT ITCQASQDVS YIYWYQQKPG KAPKPWIYRT SNLATGVPSR
FSGSGSGTDY TFTISSLQPE DIATYYCQQW DNNPYTFGQG TKLEIK

Figure 3a

```
Mu 1  QVQLKQSGAELVRPGTSVKVSCKASGYAFTNYLIEWVKQRPGQGLEWIGV     50
      ||||.|||||:.:||.|||||||||||||||||||||:|.||||||||||
Hu 1  QVQLVQSGAEVKKPGASVKVSCKASGYAFTNYLIEWVRQAPGQGLEWIGV     50

  51  INPGSGGTNYNEKFKDKATLTADKSSNTAYMQLSSLTSDDSAVYFCARRG    100
      ||||||||||||||:.:.|||||||.:||||:||.|.|||:|||:|||||
  51  INPGSGGTNYNEKFQGRVTLTADKSISTAYMELSRLRSDDTAVYYCARRG    100

  101 WDYFDYWGQGTTLTVSS    117 (SEQ ID NO:1)
      |||||||||||.:||||
  101 WDYFDYWGQGTLVTVSS    117 (SEQ ID NO:13)
```

Figure 3b

```
Mu 1   QIVLTQSPALMSTSPGEKVTMTCSASSSVSYIYWFQQKPGSSPKPWIYRT     50
       .|.|||||:.:|.|.|::||:||.||..||||||:|||||.:||||||||
Hu 1   DIQLTQSPSSLSASVGDRVTITCQASQDVSYIYWYQQKPGKAPKPWIYRT     50

  51  SNLASGVPARFSGSGSGTSYSLTISSMEAEDAATYYCQQWDNNPYTFGGG    100
      ||||:|||:|||||||||.|:.||||::.||.||||||||||||||||.|
  51  SNLATGVPSRFSGSGSGTDYTFTISSLQPEDIATYYCQQWDNNPYTFGQG    100

  101 TKLEIK    106 (SEQ ID NO:2)
      ||||||
  101 TKLEIK    106 (SEQ ID NO:14)
```

ANTIBODIES AND METHODS OF USE

RELATED INFORMATION PARAGRAPH

This application is a 35 U.S.C. 371 national stage filing of International Application No. PCT/GB2020/051588, filed on Jul. 2, 2020, which claims the benefit of U.S. Provisional Patent Application No. 62/965,450, filed on Jan. 24, 2020 and U.S. Provisional Patent Application No. 62/870,269, filed on Jul. 3, 2019, the content of each of which is hereby incorporated by reference in its entirety.

SEQUENCE LISTING

The instant application contains a Sequence Listing which has been submitted electronically in ASCII format and is hereby incorporated by reference in its entirety. Said ASCII copy, created on Dec. 23, 2021, is named OTJ-022US_Sequence_Listing.txt and is 21,860 bytes in size.

FIELD OF THE INVENTION

The present invention relates to antibodies that are capable of binding to a SLAMF6 protein, and their uses.

INTRODUCTION

Aspects of the invention include antibodies and other therapeutic proteins directed against SLAM family member 6 (SLAMF6) also known as NTB-A or CD352, nucleic acids encoding such antibodies and therapeutic proteins, methods for preparing antibodies and other therapeutic proteins, and methods for the treatment of diseases, such as cancers, by using antibodies and other therapeutic proteins directed against SLAMF6.

BACKGROUND OF THE INVENTION

The target antigen, SLAMF6 is a single-pass type I membrane protein and is a member of the immunoglobulin superfamily and of the CD2 subfamily (J Exp Med. 2001 Aug. 6; 194(3):235-46). Its activities are controlled by presence or absence of small cytoplasmic adapter proteins, SH2D1A/SAP and/or SH2D1B/EAT-2. The protein triggers cytolytic activity only in natural killer cells (NK) expressing high surface densities of natural cytotoxicity receptors (J. Exp. Med. 194:235-246(2001)). Positive signaling in NK cells implicates phosphorylation of VAV1. NK cell activation seems to depend on SH2D1B and not on SH2D1A. In conjunction with SLAMF1, SLAMF6 controls the transition between positive selection and the subsequent expansion and differentiation of the thymocytic natural killer T (NKT) cell lineage. SLAMF6 also promotes T-cell differentiation into a helper T-cell Th17 phenotype leading to increased IL-17 secretion; the costimulatory activity requires SH2D1A (J. Immunol. 177:3170-3177(2006)). It further promotes recruitment of RORC to the IL-17 promoter (J. Biol. Chem. 287:38168-38177(2012)). In conjunction with SLAMF1 and CD84/SLAMF5, SLAMF6 may be a negative regulator of the humoral immune response. In the absence of SH2D1A/SAP, SLAMF6 can transmit negative signals to $CD4^+$ T-cells and NKT cells. It also negatively regulates germinal center formation by inhibiting T-cell:B-cell adhesion; the function probably implicates increased association with PTPN6/SHP-1 via ITSMs in absence of SH2D1A/SAP.

WO2008/027739 discloses anti-NTB-A antibodies and pharmaceutical compositions comprising such antibodies.

Also described are methods of using such antibodies to bind NTB-A and treat diseases, such as hematological malignancies, which are characterised by expression of NTB-A.

WO2014/100740 and WO2017/004330 disclose antibodies, including antibody drug conjugates, that specifically bind to NTB-A and methods of using these to detect or modulate activity of an NTB-A-expressing cell. Also disclosed are methods of treatment of diseases associated with NTB-A-expressing cells, such as multiple myeloma, non-Hodgkin lymphoma and acute myeloid leukemia.

WO2015/104711 describes compositions and methods for improved T cell modulation ex vivo and in vivo and for the treatment of cancer and other pathologies. More specifically, embodiments of the invention are directed to the use of soluble NTB-A polypeptides or agonists thereof for the treatment of cancer patients, for preventing and treating cytopenia in susceptible patients, and for the ex vivo preparation of improved cell compositions.

SUMMARY

Aspects of the invention include specific antibodies directed against SLAMF6, bispecific antibodies directed against SLAMF6 and a tumor associated antigen, nucleic acids encoding such antibodies of the invention, host cells comprising such nucleic acids encoding an antibody of the invention, methods for preparing antibodies of the invention, and methods for the treatment of diseases, e.g., human cancers, including but not limited to small cell lung cancer, non-small cell lung cancer (including squamous carcinomas and adenocarcinomas) skin cancer including melanoma, breast cancer (including TNBC), colorectal cancer, gastric cancer, ovarian cancer, cervical cancer, prostate cancer, kidney cancer, liver cancer including hepatocellular carcinoma, pancreatic cancer, head and neck cancer, nasopharyngeal cancer, oesophageal cancer, bladder cancer and other uroepithelial cancers and stomach cancer, glioma, glioblastoma, testicular, thyroid, bone, gallbladder and bile ducts, uterine, adrenal cancers, sarcomas, GIST, neuroendocrine tumours, and haematological malignancies.

Described herein there is provided an antibody that binds to SLAMF6 (SEQ ID NO:11). Preferably, said antibody binds to the extracellular domain of SLAMF6 (SEQ ID NO: 12). Aspects of the invention include an antibody, or an antigen binding fragment thereof, which binds to an epitope on the SLAMF6 protein recognized by an antibody described herein, or which cross-competes for binding with an antibody described herein, and which preferably retains at least about 80%, at least about 85%, at least about 90%, at least about 91%, at least about 92%, at least about 93%, at least about 94%, at least about 95%, at least about 96%, at least about 97%, at least about 98% or at least about 99%, of the binding affinity for human SLAMF6 of an antibody described herein. In some embodiments the antibody is an isolated antibody.

Aspects of the invention include an antibody, or an antigen-binding fragment thereof, that binds to SLAMF6, said antibody comprising a heavy chain variable region comprising: a CDR-H1 sequence comprising the sequence of SEQ ID NO: 5; a CDR-H2 sequence comprising the sequence of SEQ ID NO: 6 or SEQ ID NO:15; and a CDR-H3 sequence comprising the sequence of SEQ ID NO: 7. In some embodiments, the antibody or antigen-binding fragment further comprises a light chain variable region comprising at least one CDR sequence selected from the group consisting of: CDR-L1 comprising any one of the sequences of SEQ ID NO: 8, or SEQ ID NO: 16; CDR-L2 comprising any one of the sequences of SEQ ID NO: 9, or SEQ ID NO:17; and CDR-L3 comprising the sequence of SEQ ID NO: 10. In some embodiments, the antibody, or antigen-binding fragment thereof, that binds to SLAMF6 comprises a heavy chain variable region and a light chain variable region comprising one of the 8 combinations of heavy and light chain CDRs as shown in Table 1

TABLE 1

| | Heavy Chain Variable Region CDRs | | | Light Chain Variable Region CDRs | | |
|---|---|---|---|---|---|---|
| | CDR-H1 | CDR-H2 | CDR-H3 | CDR-L1 | CDR-L2 | CDR-L3 |
| 1 | SEQ ID NO:5 | SEQ ID NO:6 | SEQ ID NO:7 | SEQ ID NO:8 | SEQ ID NO:9 | SEQ ID NO:10 |
| 2 | SEQ ID NO:5 | SEQ ID NO:15 | SEQ ID NO:7 | SEQ ID NO:8 | SEQ ID NO:9 | SEQ ID NO:10 |
| 3 | SEQ ID NO:5 | SEQ ID NO:6 | SEQ ID NO:7 | SEQ ID NO:16 | SEQ ID NO:17 | SEQ ID NO:10 |
| 4 | SEQ ID NO:5 | SEQ ID NO:15 | SEQ ID NO:7 | SEQ ID NO:16 | SEQ ID NO:17 | SEQ ID NO:10 |
| 5 | SEQ ID NO:5 | SEQ ID NO:6 | SEQ ID NO:7 | SEQ ID NO:16 | SEQ ID NO:9 | SEQ ID NO:10 |
| 6 | SEQ ID NO:5 | SEQ ID NO:15 | SEQ ID NO:7 | SEQ ID NO:16 | SEQ ID NO:9 | SEQ ID NO:10 |
| 7 | SEQ ID NO:5 | SEQ ID NO:6 | SEQ ID NO:7 | SEQ ID NO:8 | SEQ ID NO:17 | SEQ ID NO:10 |
| 8 | SEQ ID NO:5 | SEQ ID NO:15 | SEQ ID NO:7 | SEQ ID NO:8 | SEQ ID NO:17 | SEQ ID NO:10 |

In some preferred embodiments, the antibody, or antigen-binding fragment thereof, that binds to SLAMF6 comprises a heavy chain variable region comprising a CDR-H1 comprising SEQ ID NO:5; a CDR-H2 comprising SEQ ID NO:6; and a CDR-H3 comprising SEQ ID NO:7; and a light chain variable region comprising a CDR-L1 comprising SEQ ID NO:8; a CDR-L2 comprising SEQ ID NO:9; and a CDR-L3 comprising SEQ ID NO:10.

In another preferred embodiment, the antibody, or antigen-binding fragment thereof, that binds to SLAMF6 comprises a heavy chain variable region comprising a CDR-H1 comprising SEQ ID NO:5; a CDR-H2 comprising SEQ ID NO:15; and a CDR-H3 comprising SEQ ID NO:7; and a light chain variable region comprising a CDR-L1 comprising SEQ ID NO:16; a CDR-L2 comprising SEQ ID NO:17; and a CDR-L3 comprising SEQ ID NO:10.

In a further aspect, the antibodies, or antigen-binding fragments thereof, of the invention comprise variable CDRs as compared to the parent antibody described herein. Thus, the invention provides variant antibodies, or antigen-binding fragments thereof, comprising variant variable regions of a parent antibody, wherein the parent antibody, or antigen-binding fragment thereof, comprises a heavy chain variable region comprising: a CDR-H1 sequence comprising the sequence of SEQ ID NO: 5; a CDR-H2 sequence comprising the sequence of SEQ ID NO: 15; and a CDR-H3 sequence comprising the sequence of SEQ ID NO: 7; and a light chain variable region comprising a CDR-L1 comprising the sequence of SEQ ID NO: 16; CDR-L2 comprising the sequence of SEQ ID NO: 17; and CDR-L3 comprising the sequence of SEQ ID NO: 10, and wherein in one embodiment the variant antibody, or antigen-binding fragment thereof, has 1, 2, 3, 4, 5 or 6 amino acid substitutions, additions and or deletions in any one or more of; or 1, 2, 3, 4, 5, 6, 7, 8, 9, 10, 11, 12 amino acid substitutions, additions and or deletions collectively in; the set of CDR-H1, CDR-H2, CDR-H3, CDR-L1, CDR-L2 and CDR-L3, with from 1 to 5 or 1 to 4 or 1 to 3 substitutions additions or deletions of particular use, and wherein the antibody, or antigen-binding fragment thereof, retains specific binding to SLAMF6. Preferably the variations are substitutions, preferably, the substitutions are conservative substitutions or substitutions to revert an amino acid in the variable region back to the corresponding amino acid from the human germline. In a further embodiment, the variant antibody, or antigen-binding fragment thereof, of the invention comprises: a CDR-H1 sequence comprising the sequence of SEQ ID NO: 5; a CDR-H2 sequence comprising the sequence of SEQ ID NO: 15; and a CDR-H3 sequence comprising the sequence of SEQ ID NO: 7; and a light chain variable region comprising a CDR-L1 comprising the sequence of SEQ ID NO: 16; CDR-L2 comprising the sequence of SEQ ID NO: 17; and CDR-L3 comprising the sequence of SEQ ID NO: 10, wherein one or more of said CDR sequences is altered such that it is about 70%, 75%, 80%, 85%, 87%, 88%, 89%, 90%, 91%, 92%, 93%, 94%, 95%, 96%, 97%, 98%, 99% identical to the corresponding parental CDR sequence recited above.

In some embodiments there is provided an antibody, or antigen-binding fragment thereof, comprising a heavy chain variable region described in SEQ ID NO: 1 or SEQ ID NO: 13, or a sequence that is about 80%, 85%, 90%, 91%, 92%, 93%, 94%, 95%, 96%, 97%, 98%, 99% identical to SEQ ID NO: 1 or SEQ ID NO: 13 and/or a light chain variable region described in SEQ ID NO: 2, or SEQ ID NO: 14, or a sequence that is about 80%, 85%, 90%, 91%, 92%, 93%, 94%, 95%, 96%, 97%, 98%, 99% identical to SEQ ID NO: 2, or SEQ ID NO: 14. In further embodiments there is provided an antibody, or antigen-binding fragment thereof, comprising a heavy chain variable region that comprises 1, 2, 3, 4, 5, 6, 7, 8, 9, 10, 11 or 12 amino acid substitutions, additions and/or deletions compared to SEQ ID NO: 1 or SEQ ID NO: 13 and/or a light chain variable region that comprises 1, 2, 3, 4, 5, 6, 7, 8, 9, 10, 11 or 12 amino acid substitutions additions and/or deletions compared to SEQ ID NO: 2, or SEQ ID NO: 14. Preferably, the variant comprises substitutions, more preferably conservative substitutions.

It will further be apparent that the amino acid substitutions, additions and/or deletions can be within the framework regions and/or within the CDRs.

In one embodiment there is provided an antibody, or antigen-binding fragment thereof comprising a heavy chain variable region comprising the sequence of SEQ ID NO: 1, and a light chain variable region comprising the sequence of SEQ ID NO: 2.

In one embodiment there is provided an antibody, or antigen-binding fragment thereof comprising a heavy chain variable region comprising the sequence of SEQ ID NO: 13, and a light chain variable region comprising the sequence of SEQ ID NO: 14.

In one embodiment there is provided a full length antibody comprising a heavy chain sequence comprising SEQ ID NO:18 and a light chain sequence comprising SEQ ID NO: 19.

In a further aspect of the present invention there is provided an antibody, or antigen binding-fragment thereof that specifically binds to SLAMF6, said antibody or antigen binding-fragment thereof comprising the 3 heavy chain CDRs of SEQ ID NO:1 or SEQ ID NO:13 and the 3 light chain CDRs of SEQ ID NO:2, or SEQ ID NO:14 wherein the CDRs are defined by the Kabat or by the Chothia numbering system. Preferably, said antibody, or antigen binding-fragment thereof that specifically binds to SLAMF6, comprises the 3 heavy chain CDRs of SEQ ID NO:13 and the 3 light chain CDRs of SEQ ID NO:14 defined by the Kabat or by the Chothia numbering system.

SEQ ID NOs:13-19 are humanised antibody sequences based on the sequences of SEQ ID Nos: 1 and 2. The skilled person would readily understand that SEQ ID Nos: 18-19 are full length heavy and light chain sequences including the regions other than the variable regions which are required to produce a full-length functional antibody i.e. the constant and Fc regions. The skilled person will understand that the sequences are humanised by replacing amino acids from the variable region of the organism in which the antibody is produced with amino acids from the human germ line sequence in an effort to minimise the immunogenic effects of the antibodies when these are administered to human subjects. The majority of amino acid substitutions occur in the framework region however a number of amino acids from the CDRs, which occur in non-critical positions, can be substituted; such substitutions are preferably conservative in nature or revert an amino acid at a particular position to the amino acid present in the corresponding human germline. In the present case the amino acids from the CDRs which have been substituted have been identified using structural models to discriminate between paratope facing and non-paratopic residues in the CDR region. This allows the antibodies to be humanised to a higher degree than by simple CDR grafting.

In the present invention SEQ ID NO:13 comprises 2 amino acid substitutions in CDR 2 (SEQ ID NO:15) when compared to CDR2 of SEQ ID NO:1 (SEQ ID NO:6). Specifically, there is a K-Q substitution at position 16 of SEQ ID NO:6; and a D-G substitution at position 17 of SEQ ID NO:6.

In the present invention SEQ ID NO:14 comprises 3 amino acid substitutions in CDR 1 (SEQ ID NO:16) when compared to CDR1 of SEQ ID NO:2 (SEQ ID NO:8). Specifically, there is a S-Q substitution at position 1 of SEQ ID NO:8; an S-Q substitution at position 4 of SEQ ID NO:8; and an S-D substitution at position 5 of SEQ ID NO:8. SEQ ID NO:14 further comprises 1 amino acid substitution in CDR2 (SEQ ID NO:17) when compared to CDR2 of SEQ ID NO:2 (SEQ ID NO:9). Specifically, there is a S-T substitution at position 7 of SEQ ID NO:9.

It will be understood by the skilled person that these humanised sequences do not represent different, alternative, antibodies when compared to the parental antibody, but relate to the same antibody having the same characteristics which has merely been altered to correspond more closely to the human germline using structural modelling in order to minimise immunogenicity.

In some embodiments, the antibody, or antigen-binding fragment has a binding affinity ($K_D$) of 5 nM, 4 nM, 3 nM, 2 nM, 1 nM or less.

In some embodiments, an antibody, or antigen-binding fragment, is a monoclonal antibody. In some embodiments, an antibody is a chimeric, humanized, or human antibody. In some embodiments, a heavy chain variable region comprises a framework sequence. In some embodiments, at least a portion of the framework sequence comprises a human consensus framework sequence. In some embodiments, a light chain variable region comprises a framework sequence. In some embodiments, at least a portion of the framework sequence comprises a human consensus framework sequence.

Alternative strategies have also been employed to mitigate antibody effector function, including substitutions of residues in the antibody lower hinge such as L234A and L235A (LALA). These residues form part of the Fc-γ receptor binding site on the CH2 domain, and the exchange of these residues between antibody isotypes with greater or lesser effector function identified their importance in ADCC. While alanine substitutions at these sites are effective in reducing ADCC in both human and murine antibodies, these substitutions are less effective at reducing CDC activity (Lo M et al, J Biol Chem. 2017 Mar. 3; 292(9):3900-3908). In some embodiments, the antibody or antigen binding fragment is an Fc variant engineered to decrease the binding to FC gamma receptor and it results in the reduced effector function and ADCC activity.

In some embodiments, the antibody, or antigen-binding fragment, is an Fc silenced engineered IgG1 antibody or antigen-binding fragment having reduced or no binding to one or more Fc receptors. In another embodiment the antibody is an IgG4 antibody.

In some embodiments, the antibody, or antigen-binding fragment, is a bispecific antibody or antigen-binding fragment that mediates T-cell cytotoxicity and/or NK cell cytotoxicity. In some embodiments, the antibody, or antigen-binding fragment, is capable of inducing and/or enhancing activation of an immune cell. In one embodiment the immune cell is preferably a T cell. In another embodiment the immune cell is preferably an NK cell. The skilled person will understand that the term inducing and/or enhancing can refer to inducing and/or enhancing cytokine release by an immune cell and/or inducing and/or enhancing proliferation of said immune cell and/or inducing and/or enhancing cell killing activity. It will be readily apparent to the skilled person that the term induce or inducing as used in the present context means causing activation of an immune cell or increasing activation of an immune cell to above the level of activation seen in the absence of the antibody or antigen-binding fragment. The term enhancing as used in the present context refers to increasing the level of activation of an already activated immune cell.

In some embodiments, the antibody, or antigen-binding fragment, is a bispecific or multispecific antibody or antigen-binding fragment that binds to a SLAMF6 protein (e.g. SEQ ID NO:11) and binds to one or more additional binding targets preferably said additional binding targets are one or more tumor antigens. In a further embodiment the one or more additional binding targets are immunomodulatory molecules. In one embodiment the additional binding target is PD-L1. In one embodiment the antibody or antigen binding fragment thereof is bivalent. In another embodiment the antibody or antigen binding fragment thereof is quadrivalent. In another embodiment the antibody or antigen binding fragment thereof is trivalent.

In some embodiments, an antigen-binding fragment is selected from the group consisting of: Fab, Fab', $F(ab)_2$, $F(ab')_2$, Fv, FVTCR, scFv, dAb and single-domain antibody.

In another aspect of the present invention there is provided one or more nucleic acids encoding a heavy chain of an antibody of the invention and/or a light chain of an antibody of the invention. It will be understood that the heavy and light chains of the antibody of the invention can be encoded together on a single nucleic acid molecule or by two separate nucleic acid molecules.

In another aspect vectors comprising one or more of the nucleic acids of the invention are provided.

In another aspect of the present invention there is provided a host cell containing the one or more nucleic acid(s) encoding the heavy and/or light chain, or both, of the antibodies of the invention. In some embodiments said host cell is grown under conditions wherein the nucleic acid(s) is expressed. In other embodiments, a method of recovering the antibody of the invention is provided.

Aspects of the invention include methods of making an antibody, or an antigen-binding fragment thereof, the methods comprising culturing a host cell under conditions wherein the antibody, or the antigen-binding fragment, is expressed in the host cell, and optionally isolating the antibody or antigen-binding fragment.

Aspects of the invention include pharmaceutical compositions comprising an antibody, or antigen-binding fragment, as described herein and a pharmaceutically-acceptable carrier. In some embodiments, a pharmaceutical composition or medicament further comprises an effective amount of a second therapeutic agent.

In a further aspect of the present invention there is provided a method of treating a disorder, said method comprising administering to a patient in need thereof an antibody or antigen-binding fragment of the invention which binds to SLAMF6 (SEQ ID NO:11). In one embodiment the disorder is cancer.

In a further aspect there is provided a method of treating cancer comprising administering an effective amount of an antibody or antigen-binding fragment of the invention to a subject in need thereof.

In one embodiment, the antibody or antigen-binding fragment comprises a heavy chain variable region comprising a CDR-H1 comprising SEQ ID NO:5; a CDR-H2 comprising SEQ ID NO:6, or SEQ ID NO:15, and a CDR-H3 comprising SEQ ID NO:7 and a light chain variable region comprising a CDR-L1 comprising SEQ ID NO:8, or SEQ ID NO:16, a CDR-L2 comprising SEQ ID NO:9 or SEQ ID NO:17, and a CDR-L3 comprising SEQ ID NO:10.

Preferably, the heavy chain variable region comprises a CDR-H1 comprising SEQ ID NO:5, a CDR-H2 comprising SEQ ID NO:15 and a CDR-3 comprising SEQ ID NO:7.

Preferably, the light chain variable region comprises a CDR-L1 comprising SEQ ID NO:16, a CDR-L2 comprising SEQ ID NO:17 and a CDR-L3 comprising SEQ ID NO:10.

In some embodiments a method of treating cancer is provided, wherein a patient in need thereof is administered an antibody or antigen-binding fragment of the invention and wherein said antibody or antigen-binding fragment of the invention induces and/or enhances an immune response, for example, a cytotoxic T-cell response and/or an NK cell response.

In a further embodiment the antibody or antigen binding fragment thereof comprises a bispecific or multispecific antibody or antigen binding fragment thereof which binds to SLAMF6 (SEQ ID NO:11) and a tumour specific antigen.

In some embodiments, the cancer is selected from the group consisting of small cell lung cancer, non-small cell lung cancer (including squamous carcinomas and adenocarcinomas) skin cancer including melanoma, breast cancer (including TNBC), colorectal cancer, gastric cancer, ovarian cancer, cervical cancer, prostate cancer, kidney cancer, liver cancer including hepatocellular carcinoma, pancreatic cancer, head and neck cancer, nasopharyngeal cancer, oesophageal cancer, bladder cancer and other uroepithelial cancers, stomach cancer, glioma, glioblastoma, testicular, thyroid, bone, gallbladder and bile ducts, uterine, adrenal cancers, sarcomas, GIST, neuroendocrine tumours, and haematological malignancies.

According to a further aspect of the invention there is provided an antibody or antigen-binding fragment of the present invention for use in prophylaxis or therapy.

Preferably, the antibody or antigen-binding fragment is for use in the prophylaxis or therapy of cancer.

According to a further aspect of the present invention there is provided the use of an antibody or antigen-binding fragment according to the present invention in the manufacture of a medicament for the treatment of cancer.

In some embodiments, the cancer according to the previous aspects is selected from the group consisting of small cell lung cancer, non-small cell lung cancer (including squamous carcinomas and adenocarcinomas) skin cancer including melanoma, breast cancer (including TNBC), colorectal cancer, gastric cancer, ovarian cancer, cervical cancer, prostate cancer, kidney cancer, liver cancer including hepatocellular carcinoma, pancreatic cancer, head and neck cancer, nasopharyngeal cancer, oesophageal cancer, bladder cancer and other uroepithelial cancers, stomach cancer, glioma, glioblastoma, testicular, thyroid, bone, gallbladder and bile ducts, uterine, adrenal cancers, sarcomas, GIST, neuroendocrine tumours, and haematological malignancies.

BRIEF DESCRIPTION OF THE DRAWINGS

FIG. 1*a* shows the amino acid sequence of the variable region of the heavy chain of the parental murine 1B3 antibody (SEQ ID NO:1).

FIG. 1*b* shows the amino acid sequence of the variable region of the light chain of the parental murine 1B3 antibody (SEQ ID NO:2).

FIG. 2*a* shows the amino acid sequence of the variable region of the heavy chain of the humanised antibody Hu_1B3 (SEQ ID NO:13).

FIG. 2*b* shows the amino acid sequence of the variable region of the light chain of the humanised antibody Hu_1B3 (SEQ ID NO:14).

FIG. 3*a* shows a sequence alignment of the heavy chain variable region of the 1B3 parental murine antibody sequence and the humanised heavy chain variable region 1B3 sequence.

FIG. 3*b* shows a sequence alignment of the light chain variable region of the 1B3 parental murine antibody sequence and the humanised light chain variable region Hu_1B3 sequence.

FIGS. 21*a* and 21*b* show that the addition Hu_1B3 in the absence of an enabling bispecific antibody also enhances lymphocyte cytotoxicity against SKBR-3 cells.

DETAILED DESCRIPTION

Figure 4:
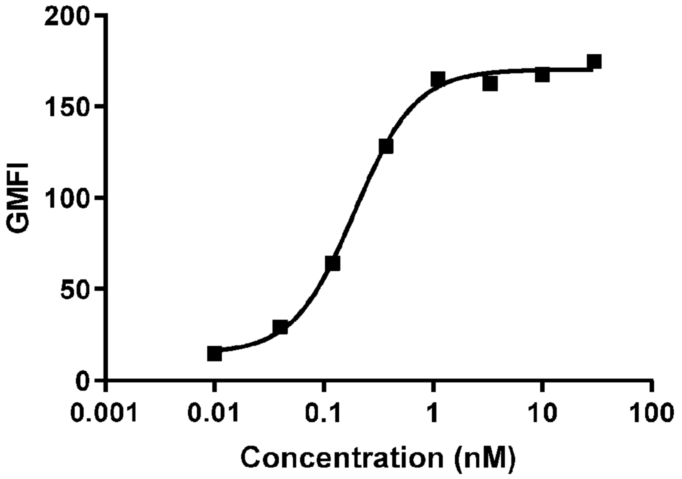
FIG. 4 shows specific dose-related binding of antibody 1B3 to 1B3 expressing Raji cells.

Aspects of the invention include antibodies directed against SLAMF6, nucleic acids encoding such antibodies, host cells comprising such nucleic acids encoding an antibody of the invention, methods for preparing anti-SLAMF6 antibodies, and methods for the treatment of diseases, such as SLAMF6-mediated disorders, e.g., human cancers, including but not limited to small cell lung cancer, non-small cell lung cancer (including squamous carcinomas and adenocarcinomas) skin cancer including melanoma, breast cancer (including TNBC), colorectal cancer, gastric cancer, ovarian cancer, cervical cancer, prostate cancer, kidney cancer, liver cancer including hepatocellular carcinoma, pancreatic cancer, head and neck cancer, nasopharyngeal cancer, oesophageal cancer, bladder cancer and other uroepithelial cancers, stomach cancer, glioma, glioblastoma, testicular, thyroid, bone, gallbladder and bile ducts, uterine, adrenal cancers, sarcomas, GIST, neuroendocrine tumours, and haematological malignancies.

It is noted that, as used herein and in the appended claims, the singular forms "a", "an", and "the" include plural references unless the context clearly dictates otherwise. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual aspects described and illustrated herein has discrete components and features which can be readily separated from or combined with the features of any of the other several aspects without departing from the scope or spirit of the present invention. Any recited method can be carried out in the order of events recited or in any other order which is logically possible.

Definitions

For purposes of interpreting this specification, the following definitions will apply and whenever appropriate, terms used in the singular will also include the plural and vice versa. The term "SLAMF6", as used herein, refers to any native SLAMF6 protein from any vertebrate source, including mammals such as primates (e.g., humans, primates, and rodents (e.g., mice and rats)), unless otherwise indicated. The SLAMF6 protein can also be referred to as a SLAMF6-like protein. The amino acid sequence of human SLAMF6 is provided herein in SEQ ID NO: 11.

The term "SLAMF6" encompasses "full-length" unprocessed SLAMF6 as well as any form of SLAMF6 that results from processing in the cell. The term also encompasses naturally occurring variants of SLAMF6, e.g., splice variants, allelic variants and isoforms. The term specifically includes naturally-occurring truncated or secreted forms of the SLAMF6 polypeptide (e.g., an extracellular domain sequence). The SLAMF6 polypeptides described herein may be isolated from a variety of sources, such as from human tissue types or from another source or prepared by recombinant or synthetic methods. A "native sequence SLAMF6 polypeptide" comprises a polypeptide having the same amino acid sequence as the corresponding SLAMF6 polypeptide derived from nature. Such native sequence SLAMF6 polypeptides can be isolated from nature or can be produced by recombinant or synthetic means. The term "SLAMF6 epitope" as used herein refers to an epitope bound by an antibody comprising at least one or more of the CDR sequences described herein, and/or as exemplified by the binding profile of an anti-SLAMF6 antibody as illustrated in the examples.

The term "antibody" is used in the broadest sense and specifically covers, for example, single anti-SLAMF6 monoclonal antibodies (including agonist, antagonist, neutralizing antibodies, full length or intact monoclonal antibodies), anti-SLAMF6 antibody compositions with polyepitopic specificity, polyclonal antibodies, multivalent antibodies, multispecific antibodies (e.g., bispecific antibodies so long as they exhibit the desired biological activity), formed from at least two intact antibodies, single chain anti-SLAMF6 antibodies, and antigen binding fragments of anti-SLAMF6 antibodies, including Fab, Fab', F(ab')2 and Fv and FV-TCR fragments, diabodies, single domain antibodies (sdAbs), as long as they exhibit the desired biological or immunological activity. The term "immunoglobulin" (Ig) is used interchangeably with the term "antibody" herein. An antibody can be chimeric, human, humanized and/or affinity matured. It will be appreciated by those of ordinary skill in the art that in some embodiments at a minimum antibodies contain a set of 6 CDRs as defined herein; they include, but are not limited to, traditional antibodies (including both monoclonal and polyclonal antibodies), humanized, human and/or chimeric antibodies, antibody fragments, engineered antibodies (e.g., with amino acid modifications as outlined below), multispecific antibodies (including bispecific antibodies), and other analogues known in the art and discussed herein.

It will be understood that in other embodiments the term antibody as used herein refers to structures which do not comprise 6 CDRs; including, but not limited to, Nanobody®, Unibody® and scFv fragments.

The term "anti-SLAMF6 antibody", "SLAMF6 antibody", or "an antibody that binds to SLAMF6" refers to an antibody that is capable of binding SLAMF6 with sufficient affinity such that the antibody is useful as a diagnostic and/or therapeutic agent in targeting SLAMF6. In certain embodiments, an anti-SLAMF6 antibody binds to an epitope of SLAMF6 that is conserved among SLAMF6 from different species.

An "isolated antibody" is one which has been identified and separated and/or recovered from a component of its environment. Contaminant components of its environment are materials which would interfere with therapeutic uses for the antibody, and may include enzymes, hormones, and other proteinaceous or non-proteinaceous solutes.

With regard to the binding of an antibody to a target molecule, the term "specific binding" or "specifically binds to" or is "specific for" a particular polypeptide or an epitope on a particular polypeptide target means binding that is measurably different from a non-specific interaction. Specific binding can be measured, for example, by determining binding of a molecule compared to binding of a control molecule, which generally is a molecule of similar structure that does not have binding activity.

The term "antagonist" is used in the broadest sense, and includes any molecule that partially or fully blocks, inhibits, or neutralizes a biological activity of a native SLAMF6 polypeptide. Suitable antagonist molecules specifically include antagonist antibodies or antibody fragments, fragments or amino acid sequence variants of native SLAMF6 polypeptides, peptides, antisense oligonucleotides, small organic molecules, etc. Methods for identifying antagonists of a SLAMF6 polypeptide, may comprise contacting an SLAMF6 polypeptide with a candidate antagonist molecule and measuring a detectable change in one or more biological activities normally associated with the SLAMF6 polypeptide.

The term "agonist" is used in the broadest sense, and includes any molecule that enhances a biological activity of a native SLAMF6 polypeptide. Suitable agonist molecules specifically include agonist antibodies or antibody fragments, fragments or amino acid sequence variants of SLAMF6 ligand polypeptides, peptides, antisense oligonucleotides, small organic molecules, etc. Methods for identifying agonists of a SLAMF6 polypeptide, may comprise contacting a SLAMF6 polypeptide with a candidate agonist molecule and measuring a detectable change in one or more biological activities normally associated with the SLAMF6 polypeptide.

"Tumor", as used herein, refers to all neoplastic cell growth and proliferation, whether malignant or benign, and all pre-cancerous and cancerous cells and tissues.

The terms "predictive" and "prognostic" as used herein are also interchangeable, in the sense of meaning that the methods for prediction or prognostication are to allow the person practicing the method to select patients that are deemed (usually in advance of treatment, but not necessarily) more likely to respond to treatment with an anti-cancer agent, including an anti-SLAMF6 antibody.

SLAMF6 Proteins

According to UNIPROT, SLAMF6 is a single pass type I membrane protein of the immunoglobulin superfamily and of the CD2 subfamily. The protein consists of an extracellular domain between amino acids 22-226 of SEQ ID No: 11, one transmembrane region between amino acids 227-247 and one cytoplasmic region between amino acids 248-331.

In some embodiments, an antibody of the invention binds to human SLAMF6. "Human SLAMF6" or "Human SLAMF6 protein" as used herein refers to the protein of SEQ ID NO:11, as defined herein.

An antibody in accordance with embodiments of the invention may, in certain cases, cross-react with a SLAMF6 protein from a species other than a human. For example, to facilitate pre-clinical and toxicology testing, an antibody of the invention may cross react with murine or primate SLAMF6 proteins. Alternatively, in certain embodiments, an antibody may be specific for a human SLAMF6 protein and may not exhibit species or other types of non-human cross-reactivity.

Antibodies

Aspects of the invention include anti-SLAMF6 antibodies, generally therapeutic and/or diagnostic antibodies, as described herein. Antibodies that find use in the methods of the present invention can take on any of a number of formats as described herein, including traditional antibodies as well as antibody derivatives, antigen-binding fragments and mimetics, as further described herein. In some embodiments, an antibody has one or more CDRs selected from a set of 6 CDRs as defined herein (including small numbers of amino acid changes as described herein). As reviewed above, the term "antibody" as used herein refers to a variety of structures.

In some embodiments, IgG isotypes are used in the present invention. In one embodiment Fc silenced IgG1 isotype antibodies are used. In another embodiment IgG4 isotype antibodies are used.

The amino-terminal portion of each chain of an antibody includes a variable region of about 100 to 110 or more amino acids primarily responsible for antigen recognition. In the variable region, three loops are gathered for each of the V domains of the heavy chain and light chain to form an antigen-binding site. Each of the loops is referred to as a complementarity-determining region (hereinafter referred to as a "CDR"), in which the variation in the amino acid sequence is most significant. "Variable" refers to the fact that certain segments of the variable region differ extensively in sequence among antibodies.

Variability within the variable region is not evenly distributed. Instead, the V regions consist of relatively invariant stretches called framework regions (FRs) of 15-30 amino acids separated by shorter regions of extreme variability called "hypervariable regions" that are each 9-15 amino acids long or longer.

Each VH and VL is composed of three hypervariable regions ("complementary determining regions," "CDRs") and four FRs, arranged from amino-terminus to carboxy-terminus in the following order: FR1-CDR1-FR2-CDR2-FR3-CDR3-FR4.

The hypervariable region generally encompasses amino acid residues from about amino acid residues 24-34 (CDR-L1; "L" denotes light chain), 50-56 (CDR-L2) and 89-97 (CDR-L3) in the light chain variable region and around about 31-35B (CDR-H1; "H" denotes heavy chain), 50-65 (CDR-H2), and 95-102 (CDR-H3) in the heavy chain variable region; Kabat et al., SEQUENCES OF PROTEINS OF IMMUNOLOGICAL INTEREST, 5th Ed. Public Health Service, National Institutes of Health, Bethesda, Md. (1991) and/or those residues forming a hypervariable loop (e.g., residues 26-32 (CDR-L1), 50-52 (CDR-L2) and 91-96 (CDR-L3) in the light chain variable region and 26-32 (CDR-H1), 53-55 (CDR-H2) and 96-101 (CDR-H3) in the heavy chain variable region; Chothia and Lesk (1987) J. Mol. Biol. 196:901-917. Specific CDRs of the invention are described below.

Throughout the present specification, the Kabat numbering system is generally used when referring to a residue in the variable domain (approximately, residues 1-107 of the light chain variable region and residues 1-113 of the heavy chain variable region) (e.g., Kabat et al., supra (1991)).

The CDRs contribute to the formation of the antigen-binding, or more specifically, epitope binding site of antibodies. A single antigen may have more than one epitope.

In the IgG subclass of immunoglobulins, there are several immunoglobulin domains in the heavy chain. By "immunoglobulin (Ig) domain" herein is meant a region of an immunoglobulin having a distinct tertiary structure. Of interest in the present invention are the heavy chain domains, including, the constant heavy (CH) domains and the hinge domains. In the context of IgG antibodies, the IgG isotypes each have three CH regions.

Another type of Ig domain of the heavy chain is the hinge region. By "hinge" or "hinge region" or "antibody hinge region" or "immunoglobulin hinge region" herein is meant the flexible polypeptide comprising the amino acids between the first and second constant domains of an antibody.

Of particular interest in the present invention are the Fc regions. By "Fc" or "Fc region" or "Fc domain" as used herein is meant the polypeptide comprising the constant region of an antibody excluding the first constant region immunoglobulin domain and in some cases, part of the hinge. Thus Fc refers to the last two constant region immunoglobulin domains of IgA, IgD, and IgG, the last three constant region immunoglobulin domains of IgE and IgM, and the flexible hinge N-terminal to these domains. For IgA and IgM, Fc may include the J chain. For IgG, the Fc domain comprises immunoglobulin domains Cγ2 and Cγ3 (Cγ2 and Cγ3) and the lower hinge region between Cγ1 (Cγ1) and Cγ2 (Cγ2). Although the boundaries of the Fc region may vary, the human IgG heavy chain Fc region is usually defined to include residues C226 or P230 to its carboxyl-terminus, wherein the numbering is according to the EU index as in Kabat. In some embodiments, amino acid modifications are made to the Fc region, for example to alter binding to one or more FcγR receptors or to the FcRn receptor. In some embodiments, the antibodies are full length. By "full length antibody" herein is meant the structure that constitutes the natural biological form of an antibody, including variable and constant regions, optionally including one or more modifications as outlined herein.

Alternatively, the antibodies can be a variety of structures, including, but not limited to, antigen-binding fragments, monoclonal antibodies, bispecific antibodies, minibodies, domain antibodies, synthetic antibodies (sometimes referred to herein as "antibody mimetics"), chimeric antibodies, humanized antibodies, antibody fusions (sometimes referred to as "antibody conjugates"), and antigen binding fragments of each, respectively. Structures that rely on the use of a set of CDRs are included within the definition of "antibody".

In one embodiment, an antibody is an antigen-binding fragment. Specific antigen-binding antibody fragments include, but are not limited to, (i) the Fab fragment consisting of VL, VH, CL and CH1 domains, (ii) the Fd fragment consisting of the VH and CH1 domains, (iii) the Fv fragment consisting of the VL and VH domains of a single antibody; (iv) the dAb fragment (Ward et al., 1989, Nature 341:544-546, entirely incorporated by reference) which consists of a single variable region, (v) isolated CDR regions, (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al., 1988, Science 242:423-426, Huston et al., 1988, Proc. Natl. Acad. Sci. U.S.A. 85:5879-5883, entirely incorporated by reference), (viii) bispecific single chain Fv (WO 03/11161, hereby incorporated by reference) and (ix) "diabodies" or "triabodies", multivalent or multispecific fragments constructed by gene fusion (Tomlinson et. al., 2000, Methods Enzymol. 326:461-479; WO94/13804; Holliger et al., 1993, Proc. Natl. Acad. Sci. U.S.A. 90:6444-6448, all incorporated by reference in their entirety).

Chimeric and Humanized Antibodies

In some embodiments, an antibody can be a mixture from different species, e.g., a chimeric antibody and/or a humanized antibody. That is, in the present invention, the CDR sets can be used with framework and constant regions other than those specifically described by sequence herein.

In general, both "chimeric antibodies" and "humanized antibodies" refer to antibodies that combine regions from more than one species. For example, "chimeric antibodies" traditionally comprise variable region(s) from a mouse (or rat, in some cases) and the constant region(s) from a human. "Humanized antibodies" generally refer to non-human antibodies that have had the variable-domain framework regions swapped for sequences found in human antibodies. Generally, in a humanized antibody, the entire antibody, except the CDRs, is encoded by a polynucleotide of human origin or is identical to such an antibody except within its CDRs. The CDRs, some or all of which are encoded by nucleic acids originating in a non-human organism, are grafted into the beta-sheet framework of a human antibody variable region to create an antibody, the specificity of which is determined by the engrafted CDRs. The creation of such antibodies is described in, e.g., WO 92/11018, Jones, 1986, Nature 321:522-525, Verhoeyen et al., 1988, Science 239:1534-1536, all entirely incorporated by reference." In one embodiment, the antibodies of the invention can be multispecific antibodies, and notably bispecific antibodies, also sometimes referred to as "diabodies". These are antibodies that bind to two (or more) different antigens, or different epitopes on the same antigen. Diabodies can be manufactured in a variety of ways known in the art (Holliger and Winter, 1993, Current Opinion Biotechnol. 4:446-449, entirely incorporated by reference), e.g., prepared chemically or from hybrid hybridomas.

In one embodiment, the antibody is a minibody. Minibodies are minimized antibody-like proteins comprising an scFv joined to a CH3 domain. Hu et al., 1996, Cancer Res. 56:3055-3061, entirely incorporated by reference. In some cases, the scFv can be joined to the Fc region, and may include some or the entire hinge region. It should be noted that minibodies are included within the definition of "antibody" despite the fact it does not have a full set of CDRs.

The antibodies of the present invention are generally isolated or recombinant.

In some embodiments, the antibodies of the invention are recombinant proteins, isolated proteins or substantially pure proteins. An "isolated" protein is unaccompanied by at least some of the material with which it is normally associated in its natural state, for example constituting at least about 5%, or at least about 50% by weight of the total protein in a given sample. It is understood that the isolated protein may constitute from 5 to 99.9% by weight of the total protein content depending on the circumstances. For example, the protein may be made at a significantly higher concentration through the use of an inducible promoter or high expression promoter, such that the protein is made at increased concentration levels. In the case of recombinant proteins, the definition includes the production of an antibody in a wide variety of organisms and/or host cells that are known in the art in which it is not naturally produced. Ordinarily, an isolated polypeptide will be prepared by at least one purification step. An "isolated antibody," refers to an antibody which is substantially free of other antibodies having different antigenic specificities. For instance, an isolated antibody that specifically binds to SLAMF6 is substantially free of antibodies that specifically bind antigens other than SLAMF6.

Isolated monoclonal antibodies, having different specificities, can be combined in a well-defined composition. Thus for example, an antibody of the invention can optionally and individually be included or excluded in a formulation, as is further discussed below. Specific binding for a particular antigen or an epitope can be exhibited, for example, by an antibody having a $K_D$ for an antigen or epitope of at least about $10^{-4}$ M, at least about $10^{-5}$ M, at least about $10^{-6}$ M, at least about $10^{-7}$ M, at least about $10^{-8}$ M, at least about $10^{-9}$ M, alternatively at least about $10^{-10}$ M, at least about $10^{-11}$ M, at least about $10^{-12}$ M, or greater, where $K_D$ refers to a dissociation rate of a particular antibody-antigen interaction. Typically, an antibody that specifically binds an antigen will have a $K_D$ that is 20-, 50-, 100-, 500-, 1000-, 5,000-, 10,000- or more times lower for the antigen or epitope relative to a control molecule.

Also, specific binding for a particular antigen or an epitope can be exhibited, for example, by an antibody having a $K_A$ or $K_a$ for an antigen or epitope of at least 20-, 50-, 100-, 500-, 1000-, 5,000-, 10,000- or more times greater for the epitope relative to a control, where $K_A$ or $K_a$ refers to an association rate of a particular antibody-antigen interaction.

Standard assays to evaluate the binding ability of the antibodies toward SLAMF6 can be done on the protein or cellular level and are known in the art, including for example, ELISAs, Western blots, RIAs, Octet®, BIAcore® assays and flow cytometry analysis. Suitable assays are described in detail in the Examples. The binding kinetics (e.g., binding affinity) of the antibodies also can be assessed by standard assays known in the art, such as by Biacore® or Octet® system analysis.

SLAMF6 Antibodies

The present invention provides SLAMF6 antibodies that bind to a SLAMF6 polypeptide or portion thereof. An example of a SLAMF6 amino acid sequence is provided in SEQ ID NO: 11. The subject SLAMF6 antibodies can induce or enhance immune cell activation, for example, T cell activation and/or NK cell activation, to enhance the immune response in the tumor. These antibodies are referred to herein either as "anti-SLAMF6" antibodies or, for ease of description, "SLAMF6 antibodies".

In some embodiments, a subject SLAMF6 antibody can induce and/or enhance cytokine release or proliferation upon contact with T cells, particularly CD4+ or CD8+ T cells which express SLAMF6 on their surface. Cytokine release or T cell proliferation in this context can be measured in several ways. In one embodiment, a SLAMF6 antibody of the invention is contacted with activated T cells, using standard assays such as ELISA. In a further embodiment a subject SLAMF6 antibody can induce and/or enhance NK cell activation and killing.

In one embodiment, the antibody is an antibody comprising the following CDRs; in addition, as discussed below, these CDR sequences can also contain a limited number of amino acid variants as previously described:

| CDR | SEQ ID NO: |
|---|---|
| 1B3_VH_CDR1 | SEQ ID NO:5 |
| 1B3_VH_CDR2 | SEQ ID NO:15 |
| 1B3_VH_CDR3 | SEQ ID NO:7 |
| 1B3_VL_CDR1 | SEQ ID NO:16 |
| 1B3_VL_CDR2 | SEQ ID NO:17 |
| 1B3_VL_CDR3 | SEQ ID NO:10 |

In some embodiments, an antibody comprises an amino acid sequence of at least one or more of the CDR sequences provided in SEQ ID NOS: 5, 15, 7, 16, 17 and 10. In some embodiments, an antibody comprises an amino acid sequence that is at least about 75%, 80%, 85%, 90%, 95%, 96%, 97%, 98% or 99% identical to an amino acid sequence of one or more of the CDR sequences provided in SEQ ID NOS: 5, 15, 7, 16, 17 and 10.

Disclosed herein are also variable heavy and light chains that comprise the CDR sets of the invention, as well as full length heavy and light chains (e.g., comprising constant regions as well). As will be appreciated by those in the art, the CDR sets of the invention can be incorporated into murine, humanized or human constant regions (including framework regions). Aspects of the invention include heavy chain variable regions and light chain variable regions that are at least about 80%, 85%, 90%, 95%, 96%, 97%, 98% or 99% identical to the heavy chain variable region sequence (SEQ ID NO: 13) and light chain variable region sequence (SEQ ID NO: 14) disclosed herein.

In some embodiments, the invention provides antibodies that bind to the same epitope on human SLAMF6 as, or that cross compete with, the SLAMF6monoclonal antibody of the invention described herein (i.e., antibodies that have the ability to cross-compete for binding to an SLAMF6protein with the monoclonal antibody of the invention described herein). It will be understood that for an antibody to be considered to cross compete, it does not necessarily completely block binding of the reference antibody. In some embodiments, binding of a reference antibody is reduced by at least about 10, 20, 30, 40, 50, 60, 70, 75, 80, 85, 90, 95, 97, 98 or 99%.

Antibody Modifications

The present invention further provides variant antibodies, sometimes referred to as "antibody derivatives" or "antibody analogues". That is, there are a number of modifications that can be made to an antibody of the invention, including, but not limited to, amino acid modifications in the CDRs (affinity maturation), amino acid modifications in the Fc region, glycosylation variants, and covalent modifications of other types (e.g., for attachment of drug conjugates, etc.).

By "variant" is meant a polypeptide sequence that differs from that of a parent polypeptide by virtue of at least one amino acid modification. In some embodiments, a parent polypeptide is either a full length variable heavy or light chain, listed in SEQ ID NOS: 1 or 2, 13 or 14, or is one or more of the CDR sequences disclosed in any of SEQ ID NOS: 5 to 10, 15, 16 or 17. In some embodiments, an amino acid modification can include a substitution, insertion and/or deletion, with the former being preferred in many cases. In some embodiments, a substitution can be a conservative substitution.

In general, variants can include any number of modifications, as long as the function of the antibody is still present, as described herein. For example, an antibody should still specifically bind to human SLAMF6. Similarly, if amino acid variants are generated within the Fc region, for example, the variant antibodies should maintain the required receptor binding functions for the particular application or indication of the antibody.

"Variants" of the subject antibodies can be made to have amino acid variations, as described herein, in either one or more of the listed CDR sequences, in one or more of the framework regions, or in one or more of the constant regions (e.g., in the Fc region) of the antibody.

In some embodiments, 1, 2, 3, 4, 5, 6, 7, 8, 9 or 10 amino acid modifications as compared to the parental sequence are generally utilized as often the goal is to alter function with a minimal number of modifications. In some embodiments, there are from 1 to 5 (1, 2, 3, 4 or 5) modifications (e.g., individual amino acid substitutions, insertions and/or deletions), with from 1-2, 1-3 and 1-4 also finding use in many embodiments. For example, in some embodiments, one or more of the CDR sequences of the antibodies of the invention may individually comprise one or more, for example, 1, 2, 3, 4 or 5 amino acid modifications, preferably 1-4, 1-3, 1 or 2 modifications. Generally no more than from 4, 5, 6, 7, 8, 9 or 10 changes are made within a set of CDRs.

It should be noted that the number of amino acid modifications may be within functional domains: for example, it may be desirable to have from 1-5 modifications in the Fc region of a wild-type or engineered protein, as well as from 1 to 5 modifications in the Fv region, for example. A variant polypeptide sequence will preferably possess at least about 75%, 80%, 85%, 90%, 91%, 92%, 93%, 94%, 95%, 96, 97%, 98% or 99% identity to the parent sequences (e.g., the variable region sequences, the constant region sequences, and/or the heavy and light chain sequences and/or the CDRs of, for example, antibody 1B3).

By "amino acid substitution" or "substitution" herein is meant the replacement of an amino acid at a particular position in a parent polypeptide sequence with another amino acid. By "amino acid insertion" or "insertion" as used herein is meant the addition of an amino acid at a particular position in a parent polypeptide sequence. By "amino acid deletion" or "deletion" as used herein is meant the removal of an amino acid at a particular position in a parent polypeptide sequence.

By "parent polypeptide", "parent protein", "precursor polypeptide", or "precursor protein" as used herein is meant an unmodified polypeptide that is subsequently modified to generate a variant. In general, a parent polypeptide as used herein may refer to 1B3 polypeptides, e.g. the 1B3 $V_H$ or $V_L$ chains or the CDR sequences. Accordingly, by "parent antibody" as used herein is meant an antibody that is modified to generate a variant antibody.

By "wild type" or "WT" or "native" herein is meant an amino acid sequence or a nucleotide sequence that is found in nature, including allelic variations. A WT protein, polypeptide, antibody, immunoglobulin, IgG, etc. has an amino acid sequence or a nucleotide sequence that has not been intentionally modified.

By "variant Fc region" herein is meant an Fc sequence that differs from that of a wild-type Fc sequence by virtue of at least one amino acid modification. Fc variant may refer to the Fc polypeptide itself, compositions comprising the Fc variant polypeptide, or the amino acid sequence.

In some embodiments, an anti-SLAMF6 antibody of the invention is composed of a variant Fc domain. As is known in the art, the Fc region of an antibody interacts with a number of Fc receptors and ligands, imparting an array of important functional capabilities referred to as effector functions. Suitable modifications can be made at one or more positions and in particular for specific amino acid substitutions that decrease or silence binding to Fc receptors.

In addition to the modifications outlined above, other modifications can be made. For example, the molecules may be stabilized by the incorporation of disulphide bridges linking the VH and VL domains (Reiter et al., 1996, Nature Biotech. 14:1239-1245, entirely incorporated by reference).

In addition, modifications at cysteines are particularly useful in antibody-drug conjugate (ADC) applications, further described below. In some embodiments, the constant region of the antibodies can be engineered to contain one or more cysteines that are particularly "thiol reactive", so as to allow more specific and controlled placement of the drug moiety. See for example U.S. Pat. No. 7,521,541, incorporated by reference in its entirety herein.

In addition, there are a variety of covalent modifications of antibodies that can be made as outlined below.

Covalent modifications of antibodies are included within the scope of this invention, and are generally, but not always, done post-translationally. For example, several types of covalent modifications of the antibody are introduced into the molecule by reacting specific amino acid residues of the antibody with an organic derivatizing agent that is capable of reacting with selected side chains or the N- or C-terminal residues.

In addition, as will be appreciated by those in the art, labels (including fluorescent, enzymatic, magnetic, radioactive, etc., can all be added to the antibodies (as well as the other compositions of the invention).

Bispecific Molecules

In another aspect, the present invention includes bispecific and multispecific molecules comprising an anti-SLAMF6 antibody, or a fragment thereof, of the invention. An antibody of the invention, or antigen-binding portion thereof, can be derivatized or linked to another functional molecule, e.g. another peptide or protein (e.g., another antibody or ligand for a receptor) to generate a bispecific molecule that binds to two different binding sites or target molecules. In some embodiments, an antibody of the invention, or an antigen-binding portion thereof, can be derivatized or linked to at least two functional molecules, e.g., other peptides or proteins (e.g., other antibodies or ligands for a receptor) to generate a multispecific molecule that binds to at least three different binding sites or target molecules. To create a bispecific or multispecific molecule of the invention, an antibody of the invention can be functionally linked (e.g., by chemical coupling, genetic fusion, noncovalent association or otherwise) to one or more other binding molecules, such as another antibody, antibody fragment, peptide or binding mimetic, such that a bispecific or multispecific molecule results.

Accordingly, the present invention includes bispecific molecules comprising at least one first binding domain for a first target epitope (i.e., SLAMF6) and a second binding domain for a second target epitope. The second target epitope may be present on the same target protein as that bound by the first binding specificity; or the second target epitope may be present on a different target protein to that bound by the first binding specificity. The second target epitope may be present on the same cell as the first target epitope (i.e., SLAMF6); or the second target epitope may be present on a target which is not displayed by the cell which displays the first target epitope. As used herein, the term "binding specificity" refers to a moiety comprising at least one antibody variable domain.

In another embodiment of the invention, the second target epitope is present on a tumor cell. Therefore, aspects of the invention include bispecific molecules capable of binding both to SLAMF6-expressing effector cells (e.g., SLAMF6-expressing cytotoxic T cells), and to tumor cells expressing a second target epitope.

In one embodiment, a bispecific antibody of the invention can have a total of either two or three antibody variable domains, wherein a first portion of the bispecific antibody is capable of recruiting the activity of a human immune effector cell by specifically binding to an effector antigen located on the human immune effector cell, in which the effector antigen is SLAMF6, said first portion consisting of at least one antibody variable domain, and a second portion of the bispecific antibody is capable of specifically binding to a target antigen other than the effector antigen, said target antigen being located on a target cell other than said human immune effector cell, and said second portion comprising at least one antibody variable domains.

In an embodiment of the invention in which a binding protein is multispecific, a molecule can further include a third binding specificity, in addition to an anti-tumor, binding specificity and an anti-SLAMF6 binding specificity. In one embodiment, a third binding specificity is an anti-enhancement factor (EF) portion, e.g., a molecule which binds to a surface protein involved in cytotoxic activity and thereby increases the immune response against the target cell. The "anti-enhancement factor portion" can be an antibody, functional antibody fragment, or a ligand that binds to a given molecule, e.g., an antigen or a receptor, and thereby results in an enhancement of the effect of the binding determinants for the target cell antigen. The "anti-enhancement factor portion" can bind a target cell antigen. Alternatively, the anti-enhancement factor portion can bind to an entity that is different from the entity to which the first and second binding specificities bind. For example, the anti-enhancement factor portion can bind a cytotoxic T-cell (e.g., via CD2, CD3, CD8, CD28, CD4, CD40, ICAM-1 or other immune cell that results in an increased immune response against the target cell).

In one embodiment, a bispecific protein of the invention comprises as a binding specificity at least one antibody, or an antigen binding fragment thereof, including, e.g., an Fab, Fab', $F(ab')_2$, Fv, FVTCR, Fd, dAb or a single chain Fv. The antibody may also be a light chain or heavy chain dimer, or any minimal fragment thereof such as an Fv or a single chain construct as described in U.S. Pat. No. 4,946,778, the contents of which is expressly incorporated by reference.

In some embodiments, an antibody that can be employed in a bispecific molecule of the invention is a rat, murine, human, chimeric or humanized monoclonal antibody. Binding of the bispecific molecules to their specific targets can be confirmed by, for example, enzyme-linked immunosorbent assay (ELISA), radioimmunoassay (RIA), FACS analysis, bioassay (e.g. growth inhibition), or Western Blot assay. Each of these assays generally detects the presence of protein-antibody complexes of particular interest by employing a labelled reagent (e.g. an antibody) specific for the complex of interest.

In one embodiment of the present invention, the bispecific antibody is a tetravalent antibody which contains four antigen binding regions. In a preferred embodiment, the antibody comprises two Fab domains targeting a first antigen and each consisting of the Heavy and Light chain Fab regions. These are arranged in the same conformation as in Fabs of native IgG. The antibody further comprises two chimeric Fab domains targeting a second antigen these consist of two chimeric polypeptide domains each comprising a chimeric "heavy" chain comprising a Variable Heavy chain domain, which is linked via its C-terminus to the N-terminus of the constant region of the alpha, or beta, chain of a T Cell Receptor (TCR), and a chimeric "light" chain comprising of the Variable Light chain domain, which is linked via its C-terminus to the N-terminus of the constant region of the beta, or alpha, chain of a TCR, respectively. The chimeric "heavy" and "light" chains are arranged into chimeric Fab domains, which are linked to the native Fab domains by attaching the C-terminus of the constant region of the alpha- or beta-chains of the TCR of the chimeric "heavy" chain to the N-terminus of the variable region of the heavy chain of the native Fab domain. Thus, the overall symmetric structure produces bispecific antibodies targeting each of the two different antigens in a bivalent fashion, so that the native Fab domain targeting the first antigen and the chimeric Fab domain targeting the second antigen are present on both arms of such a tetravalent antibody.

In another embodiment, the chimeric Fab domains are located proximal to the Fc domain, so that the C-terminus of the constant region of the alpha- or beta-chains of the constant region of the TCR comprising the chimeric "heavy" chain is attached to the N-terminus of the native hinge and the native Fab domains are located distal to the Fc domain, so that the C-terminus of the CH1 domain of the heavy chain comprising the native Fab domain is attached to the N-terminus of the variable heavy chain comprising the chimeric Fab domain. In another embodiment, asymmetric trivalent formats are employed, which are comprised of two different antibody arms, so that one arm has a single Fab domain (native or chimeric) and the second arm of the bispecific antibody possesses both Fab domains (native and chimeric) as described above. Heterodimerization of two different arms is enabled via antibody engineering in the Fc domain, as described in the art (e.g. knobs-into-wholes, electrostatic steering, etc).

In yet another embodiment an asymmetric bivalent format may be employed, which is comprised of two different antibody arms, so that one arm has a single Fab domain, native or chimeric, and the other arm also has a single Fab binding domain, chimeric or native, respectively. Heterodimerization of two different arms is enabled via antibody engineering in the Fc domain, well described in the art (e.g. knobs-into-wholes, electrostatic steering, etc).

Glycosylation

Another type of covalent modification is alterations in glycosylation. For example, an aglycosylated antibody can be made (i.e., an antibody that lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861 by Co et al., and can be accomplished by removing the asparagine at position 297.

Another type of covalent modification of the antibody comprises linking the antibody to various non-proteinaceous polymers, including, but not limited to, various polyols such as polyethylene glycol, polypropylene glycol or polyoxyalkylenes, in the manner set forth in, for example, 2005-2006 PEG Catalog from Nektar Therapeutics (available at the Nektar website) U.S. Pat. Nos. 4,640,835; 4,496,689; 4,301,144; 4,670,417; 4,791,192 or 4,179,337, all entirely incorporated by reference. In addition, as is known in the art, amino acid substitutions may be made in various positions within the antibody to facilitate the addition of polymers such as PEG. See for example, U.S. Publication No. 2005/0114037A1, entirely incorporated by reference.

In additional embodiments, for example in the use of the antibodies of the invention for diagnostic or detection purposes, the antibodies may comprise a label. By "labelled" herein is meant that a compound has at least one moiety, element, isotope or chemical compound attached to enable the detection of the compound as described in the 6th Edition of the Molecular Probes Handbook by Richard P. Haugland, hereby expressly incorporated by reference herein.

Methods for Producing the Antibodies of the Invention

The present invention further provides methods for producing the disclosed anti-SLAMF6 antibodies. These methods encompass culturing a host cell containing isolated nucleic acid(s) encoding an antibody of the invention. As will be appreciated by those in the art, this can be done in a variety of ways, depending on the nature of the antibody. In some embodiments, in the case where the antibodies of the invention are full length traditional antibodies, for example, a host cell contains nucleic acid encoding a heavy chain variable region and a light chain variable region can be cultured under conditions such that an antibody is produced and can be isolated.

The variable heavy and light chains of the antibodies of the invention are disclosed herein (both protein and nucleic acid sequences); as will be appreciated in the art, these can be easily augmented to produce full length heavy and light chains. That is, having provided the DNA fragments encoding $V_H$ and VL segments as outlined herein, these DNA fragments can be further manipulated by standard recombinant DNA techniques, for example, to convert the variable region genes to full-length antibody chain genes, to Fab fragment genes, or to an scFv gene. In these manipulations, a VL- or $V_H$-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame.

The isolated DNA encoding the $V_H$ region can be converted to a full-length heavy chain gene by operatively linking the $V_H$-encoding DNA to another DNA molecule encoding heavy chain constant regions ($C_H1$, $C_H2$ and $C_H3$). The sequences of rat heavy chain constant region genes are known in the art (see, e.g., Kabat, E. A., et al. (1991) Sequences of Proteins of Immunological Interest, Fifth Edition, US Department of Health and Human Services, NIH Publication No. 91-3242) and DNA fragments encompassing these regions can be obtained by standard PCR amplification. The heavy chain constant region can be an IgG1, IgG2, IgG3, IgG4, IgA, IgE, IgM or IgD constant region. In one preferred embodiment, the heavy chain constant region is an IgG1 or IgG4 constant region. For a Fab fragment heavy chain gene, the $V_H$-encoding DNA can be operatively linked to another DNA molecule encoding only the heavy chain $C_H1$ constant region.

The isolated DNA encoding the VLregion can be converted to a full-length light chain gene (as well as a Fab light chain gene) by operatively linking the $V_L$-encoding DNA to another DNA molecule encoding the light chain constant region, $C_L$. The sequences of rat light chain constant region genes are known in the art (see, e.g., Kabat, E. A., et al. (1991) Sequences of Proteins of Immunological Interest, Fifth Edition, US Department of Health and Human Services, NIH Publication No. 91-3242) and DNA fragments encompassing these regions can be obtained by standard PCR amplification. In one preferred embodiment, the light chain constant region is a kappa or lambda constant region.

To create a polynucleotide sequence encoding an scFv antibody fragment, the $V_H$- and VL encoding DNA fragments are operatively linked to another fragment encoding a flexible linker, e.g., encoding the amino acid sequence $(Gly_4\text{-}Ser)_3$, such that the $V_H$ and VL sequences can be expressed as a contiguous single-chain protein, with the VL and $V_H$ regions joined by the flexible linker (see, e.g., Bird et al. (1988) Science 242:423-426; Huston et al. (1988) Proc. Natl. Acad. Sci. USA 85:5879-5883; McCafferty et al., (1990) Nature 348:552-554).

Aspects of the invention include nucleic acids that encode the antibodies of the invention. Such polynucleotides encode for both the variable and constant regions of each of the heavy and light chains, although other combinations are also contemplated by the present invention in accordance with the compositions described herein. Aspects of the invention include oligonucleotide fragments derived from the disclosed polynucleotides and nucleic acid sequences complementary to these polynucleotides.

Polynucleotides in accordance with embodiments of the invention can be in the form of or can include RNA, DNA, cDNA, genomic DNA, nucleic acid analogues, and synthetic DNA. In some embodiments, a DNA molecule may be double-stranded or single-stranded, and if single stranded, may be the coding (sense) strand or non-coding (anti-sense) strand. The coding sequence that encodes the polypeptide may be identical to the coding sequence provided herein or may be a different coding sequence, which sequence, as a result of the redundancy or degeneracy of the genetic code, encodes the same polypeptides as the DNA provided herein.

In some embodiments, nucleic acid(s) encoding the antibodies of the invention are incorporated into expression vectors, which can be extrachromosomal or designed to integrate into the genome of the host cell into which it is introduced. Expression vectors can contain any number of appropriate regulatory sequences (including, but not limited to, transcriptional and translational control sequences, promoters, ribosomal binding sites, enhancers, origins of replication, etc.) or other components (selection genes, etc.), all of which are operably linked as is well known in the art. In some cases, two nucleic acids are used and each is put into a different expression vector (e.g., a heavy chain in a first expression vector, a light chain in a second expression vector), or alternatively they can be put in the same expression vector. It will be appreciated by those skilled in the art that the design of the expression vector(s), including the selection of regulatory sequences may depend on such factors as the choice of the host cell, the level of expression of protein desired, etc.

In general, the nucleic acids and/or expression can be introduced into a suitable host cell to create a recombinant host cell using any method appropriate to the host cell selected (e.g., transformation, transfection, electroporation, infection), such that the nucleic acid molecule(s) are operably linked to one or more expression control elements (e.g., in a vector, in a construct created by processes in the cell, integrated into the host cell genome). The resulting recombinant host cell can be maintained under conditions suitable for expression (e.g., in the presence of an inducer, in a suitable non-human animal, in suitable culture media supplemented with appropriate salts, growth factors, antibiotics, nutritional supplements, etc.), whereby the encoded polypeptide(s) are produced. In some embodiments, a heavy chain and a light chain are produced in the same host cell. In some embodiments, a heavy chain is produced in one host cell and a light chain is produced in another host cell.

Mammalian cell lines available as hosts for expression are known in the art and include many immortalized cell lines available from the American Type Culture Collection (ATCC), Manassas, VA including but not limited to Chinese hamster ovary (CHO) cells, HEK 293 cells, FS293, Expi293, NSO cells, HeLa cells, baby hamster kidney (BHK) cells, monkey kidney cells (COS), human hepatocellular carcinoma cells (e.g., Hep G2), and a number of other cell lines. Non-mammalian cells including but not limited to bacterial, yeast, insect, and plants can also be used to express recombinant antibodies. In some embodiments, the antibodies can be produced in transgenic animals such as cows or chickens.

General methods for antibody molecular biology, expression, purification, and screening are well known, for example, see U.S. Pat. Nos. 4,816,567, 4,816,397, 6,331,415 and 7,923,221, as well as Antibody Engineering, edited by Kontermann & Dubel, Springer, Heidelberg, 2001 and 2010 Hayhurst & Georgiou, 2001, Curr Opin Chem Biol 5:683-689; Maynard & Georgiou, 2000, Annu Rev Biomed Eng 2:339-76; and Morrison, S. (1985) Science 229:1202.

Pharmaceutical Compositions

Aspects of the invention include a composition, e.g., a pharmaceutical composition, containing one or more (or a combination of) antibodies, or antigen-binding portion(s) thereof, of the present invention, formulated together with a pharmaceutically acceptable carrier. Such compositions may include one or a combination of (e.g., two or more different) antibodies or bispecific molecules of the invention. For example, a pharmaceutical composition of the invention can comprise a combination of antibodies that bind to different epitopes on a target antigen or that have complementary activities. Pharmaceutical compositions of the invention also can be administered in combination therapy, i.e., combined with other agents. For example, the combination therapy can include an antibody of the present invention combined with at least one other anti-tumor agent, or an anti-inflammatory or immunosuppressant agent. Examples of therapeutic agents that can be used in combination therapy are described in greater detail below in the section on uses of the antibodies of the invention.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, i.e., antibody or antibody fragment, may be coated in a material to protect the compound from the action of acids and other natural conditions that may inactivate the compound.

The pharmaceutical compounds of the invention may include one or more pharmaceutically acceptable salts. A "pharmaceutically acceptable salt" refers to a salt that retains a desired biological activity of the parent compound and does not impart any undesired toxicological effects (see, e.g., Berge, S. M., et al. (1977) J. Pharm. Sci. 66:1-19). A pharmaceutical composition of the invention also may include a pharmaceutically acceptable anti-oxidant. Examples of suitable aqueous and non-aqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminium monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the invention is contemplated. Supplementary active compounds can also be incorporated into the compositions.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

For administration of an antibody, a dosage can range from about 0.0001 to 100 mg/kg, about 0.001 to 50 mg/kg, about 0.001 to 10 mg/kg, about 0.01 to 10 mg/kg and more usually 0.01 to 5 mg/kg, of the host body weight. For example dosages can be 0.1 mg/kg, 0.2 mg/kg, 0.3 mg/kg, 0.4 mg/kg, 0.5 mg/kg, 0.75 mg/kg body weight, 1 mg/kg body weight, 3 mg/kg body weight, 4 mg/kg body weight, 5 mg/kg body weight, 7.5 mg/kg body weight or 10 mg/kg body weight or within the range of 0.1-5 mg/kg or 1-10 mg/kg. An example treatment regimen entails administration daily, on alternate days, twice per week, once per week, once every two weeks, once every three weeks, once every four weeks, once a month, once every 3 months or once every three to 6 months. Preferred dosage regimens for an anti-SLAMF6 antibody of the invention include 1 mg/kg body weight, 3 mg/kg, 5 mg/kg or 10 mg/kg body weight via intravenous administration, with the antibody being given using one of the following dosing schedules: (i) every week for six dosages, then every month; (ii) every week; (iii) 3 mg/kg body weight once followed by 1 mg/kg body weight every week.

In some methods, two or more monoclonal antibodies with different binding specificities are administered simultaneously, in which case the dosage of each antibody administered falls within the ranges indicated. In some embodiments, an antibody is administered on multiple occasions. Intervals between single dosages can be, for example, weekly, monthly, every three months or yearly. Intervals can also be irregular as indicated by measuring blood levels of antibody to the target antigen in the patient. In some embodiments, dosage is adjusted to achieve a plasma antibody concentration of about 1-1000 μg/ml and in some methods about 25-300 μg/ml.

In some embodiments, an antibody can be administered as a sustained release formulation, in which case less frequent administration is required. Dosage and frequency vary depending on the half-life of the antibody in the patient. In general, human antibodies show the longest half-life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A "therapeutically effective dosage" of an antibody of the invention preferably results in a decrease in severity of disease symptoms, an increase in frequency and duration of disease symptom-free periods, or a prevention of impairment or disability due to the disease affliction. For example, a "therapeutically effective dosage" preferably inhibits cell growth or tumor growth by at least about 10%, at least about 20%, at least about 30%, more preferably by at least about 40%, at least about 50%, even more preferably by at least about 60%, at least about 70%, and still more preferably by at least about 80%, at least about 90% or at least about 95% relative to untreated subjects. The ability of a compound to inhibit tumor growth can be evaluated in an animal model system predictive of efficacy in human tumors. Alternatively, this property of a composition can be evaluated by examining the ability of the compound to inhibit cell growth, such inhibition can be measured in vitro by assays known to the skilled practitioner. A therapeutically effective amount of a therapeutic compound can decrease tumor size, or otherwise ameliorate symptoms in a subject. One of ordinary skill in the art would be able to determine such amounts based on such factors as the subject's size, the severity of the subject's symptoms, and the particular composition or route of administration selected.

A composition of the present invention can be administered via one or more routes of administration using one or more of a variety of methods known in the art. As will be appreciated by the skilled artisan, the route and/or mode of administration will vary depending upon the desired results. Preferred routes of administration for antibodies of the invention include intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Alternatively, an antibody of the invention can be administered via a non-parenteral route, such as a topical, epidermal or mucosal route of administration, for example, intranasally, orally, vaginally, rectally, sublingually or topically.

The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art (see, e.g., Sustained and Controlled Release Drug Delivery Systems (1978) J. R. Robinson, ed., Marcel Dekker, Inc., N.Y).

In certain embodiments, a monoclonal antibody of the invention can be formulated to ensure proper distribution in vivo. For example, the blood-brain barrier (BBB) excludes many highly hydrophilic compounds. To ensure that the therapeutic compounds of the invention cross the BBB (if desired), they can be formulated, for example, in liposomes. For methods of manufacturing liposomes, see, e.g. U.S. Pat. Nos. 4,522,811; 5,374,548; and 5,399,331. The liposomes may comprise one or more moieties which are selectively transported into specific cells or organs, thus enhance targeted drug delivery (see, e.g., V. V. Ranade (1989) J. Clin. Pharmacol. 29:685). Exemplary targeting moieties include folate or biotin (see, e.g., U.S. Pat. No. 5,416,016.); mannosides (Umezawa et al. (1988) Biochem. Biophys. Res. Commun. 153:1038); antibodies (P. G. Bloeman et al. (1995) FEBS Lett. 357:140; M. Owais et al. (1995) Antimicrob. Agents Chemother. 39:180); surfactant protein A receptor (Briscoe et al. (1995) Am. J. Physiol. 1233:134); p120 (Schreier et al. (1994) J. Biol. Chem. 269:9090); see also K. Keinanen; M. L. Laukkanen (1994) FEBS Lett. 346:123; J. J. Killion; I. J. Fidler (1994) Immunomethods 4:273.

Uses and Methods

The antibodies, antibody compositions and methods of the present invention have numerous in vitro and in vivo diagnostic and therapeutic utilities involving the diagnosis and treatment of immune-mediated disorders.

In some embodiments, these molecules can be administered to cells in culture, in vitro or ex vivo, or to human subjects, e.g., in vivo, to treat, prevent and/or diagnose a variety of disorders. As used herein, the term "subject" is intended to include human and non-human animals. Non-human animals include all vertebrates, e.g., mammals, such as non-human primates, and non-mammals. Preferred subjects include human patients. When antibodies of the invention are administered together with another agent, the two can be administered in either order or simultaneously.

Given the specific binding of the antibodies of the invention for SLAMF6, the antibodies of the invention can be used to specifically detect SLAMF6 expression on the surface of immune cells and, moreover, can be used to purify SLAMF6 via immunoaffinity purification. Furthermore, given the expression of SLAMF6 on immune cells, the antibodies, antibody compositions and methods of the present invention can be used to treat a subject with a tumorigenic disorder, e.g., a disorder characterized by the presence of tumor cells, for example small cell lung cancer, non-small cell lung cancer (including squamous carcinomas and adenocarcinomas) skin cancer including melanoma, breast cancer (including TNBC), colorectal cancer, gastric cancer, ovarian cancer, cervical cancer, prostate cancer, kidney cancer, liver cancer including hepatocellular carcinoma, pancreatic cancer, head and neck cancer, nasopharyngeal cancer, oesophageal cancer, bladder cancer and other uroepithelial cancers, stomach cancer, glioma, glioblastoma, testicular, thyroid, bone, gallbladder and bile ducts, uterine, adrenal cancers, sarcomas, GIST, neuroendocrine tumours, and haematological malignancies.

In one embodiment, antibodies of the present invention are used for the treatment of cancer, for example, small cell lung cancer, non-small cell lung cancer (including squamous carcinomas and adenocarcinomas) skin cancer including melanoma, breast cancer (including TNBC), colorectal cancer, gastric cancer, ovarian cancer, cervical cancer, prostate cancer, kidney cancer, liver cancer including hepatocellular carcinoma, pancreatic cancer, head and neck cancer, nasopharyngeal cancer, oesophageal cancer, bladder cancer and other uroepithelial cancers, stomach cancer, glioma, glioblastoma, testicular, thyroid, bone, gallbladder and bile ducts, uterine, adrenal cancers, sarcomas, GIST, neuroendocrine tumours, and haematological malignancies.

In a further embodiment, the antibodies of the invention are used in the manufacture of a medicament for the treatment of cancer, for example, small cell lung cancer, non-small cell lung cancer (including squamous carcinomas and adenocarcinomas) skin cancer including melanoma, breast cancer (including TNBC), colorectal cancer, gastric cancer, ovarian cancer, cervical cancer, prostate cancer, kidney cancer, liver cancer including hepatocellular carcinoma, pancreatic cancer, head and neck cancer, nasopharyngeal cancer, oesophageal cancer, bladder cancer and other uroepithelial cancers, stomach cancer, glioma, glioblastoma, testicular, thyroid, bone, gallbladder and bile ducts, uterine, adrenal cancers, sarcomas, GIST, neuroendocrine tumours, and haematological malignancies.

In one embodiment, the antibodies (e.g., monoclonal antibodies, antibody fragments, Nanobody™, multispecific and bispecific molecules and compositions, etc.) of the invention can be used to detect levels of SLAMF6, or levels of immune cells which contain SLAMF6 on their membrane surface, which levels can then be linked to certain disease symptoms for diagnosis.

In another embodiment, the antibodies (e.g., monoclonal antibodies, multispecific and bispecific molecules and compositions) of the invention can be initially tested for binding activity associated with therapeutic or diagnostic use in vitro. For example, compositions of the invention can be tested using the flow cytometric assays described in the examples below.

In some embodiments, the antibodies (e.g., monoclonal antibodies, multispecific and bispecific molecules and compositions) of the invention have additional utility in therapy and diagnosis of diseases. For example, the monoclonal antibodies, the multispecific or bispecific molecules can be used to elicit in vivo or in vitro one or more of the following biological activities: to induce and/or enhance activation of an immune cell; to mediate phagocytosis or ADCC of a cell in the presence of human effector cells expressing SLAMF6, or to block an SLAMF6 ligand from binding to SLAMF6.

In a particular embodiment, the antibodies (e.g., monoclonal antibodies, multispecific and bispecific molecules and compositions) are used in vivo to treat, prevent or diagnose a variety of diseases. Examples of relevant diseases include, among others, human cancer tissues representing small cell lung cancer, non-small cell lung cancer (including squamous carcinomas and adenocarcinomas) skin cancer including melanoma, breast cancer (including TNBC), colorectal cancer, gastric cancer, ovarian cancer, cervical cancer, prostate cancer, kidney cancer, liver cancer including hepatocellular carcinoma, pancreatic cancer, head and neck cancer, nasopharyngeal cancer, oesophageal cancer, bladder cancer and other uroepithelial cancers, stomach cancer, glioma, glioblastoma, testicular, thyroid, bone, gallbladder and bile ducts, uterine, adrenal cancers, sarcomas, GIST, neuroendocrine tumours, and haematological malignancies.

Suitable routes of administering the antibody compositions (e.g., monoclonal antibodies, multispecific and bispecific molecules and compositions) of the invention in vivo and in vitro are well known in the art and can be selected by those of ordinary skill. For example, the antibody compositions can be administered by injection (e.g., intravenous or subcutaneous). Suitable dosages of the molecules used will depend on the age and weight of the subject and the concentration and/or formulation of the antibody composition.

As previously described, the antibodies of the invention can be co-administered with one or more additional therapeutic agents, e.g., an immunostimulatory agent, a cytotoxic agent, a radiotoxic agent or an immunosuppressive agent. An antibody can be linked to an agent (as an immunocomplex) or can be administered separate from the agent. In the latter case (separate administration), the antibody can be administered before, after or concurrently with the agent or can be co-administered with other known therapies, e.g., an anti-cancer therapy, e.g., radiation therapy. Such therapeutic agents include, among others, anti-neoplastic agents such as doxorubicin (adriamycin), cisplatin bleomycin sulfate, carmustine, chlorambucil, and cyclophosphamide hydroxyurea which, by themselves, are only effective at levels which are toxic or subtoxic to a patient. Other agents suitable for co-administration with the antibodies of the invention include other agents used for the treatment of cancers, such as Avastin® (bevacizumab), 5FU and gemcitabine. Co-administration of the anti-SLAMF6 antibodies or antigen binding fragments thereof, of the present invention with chemotherapeutic agents provides two anti-cancer agents which operate via different mechanisms which yield a cytotoxic effect to human tumor cells. Such co-administration can solve problems due to development of resistance to drugs or a change in the antigenicity of the tumor cells.

Target-specific effector cells, e.g., effector cells linked to compositions (e.g., monoclonal antibodies, multispecific and bispecific molecules) of the invention can also be used as therapeutic agents. Effector cells for targeting can be human leukocytes such as macrophages, neutrophils or monocytes. Other cells include eosinophils, natural killer cells and other IgG- or IgA-receptor bearing cells. If desired, effector cells can be obtained from the subject to be treated. The target-specific effector cells can be administered as a suspension of cells in a physiologically acceptable solution. The number of cells administered can be in the order of $10^8$-$10^9$, but will vary depending on the therapeutic purpose.

Therapy with target-specific effector cells can be performed in conjunction with other techniques. For example, anti-tumor therapy using the compositions (e.g., monoclonal antibodies, multispecific and bispecific molecules) of the invention and/or effector cells armed with these compositions can be used in conjunction with chemotherapy. Additionally, combination immunotherapy may be used to direct two distinct cytotoxic effector populations toward tumor cell rejection.

Bispecific and multispecific molecules of the invention can also be used to modulate FcγR or FcγR levels on effector cells, such as by capping and elimination of receptors on the cell surface. Mixtures of anti-Fc receptors can also be used for this purpose.

Aspects of the invention include kits comprising the antibody compositions of the invention (e.g., monoclonal antibodies, bispecific or multispecific molecules) and instructions for their use, e.g., in the treatment of cancer. The kit can further contain one or more additional reagents, such as an immunosuppressive reagent, a cytotoxic agent or a radiotoxic agent, or one or more additional antibodies of the invention (e.g., an antibody having a complementary activity which binds to an epitope in the SLAMF6 antigen distinct from the first antibody).

Accordingly, patients treated with antibody compositions of the invention can be additionally administered (prior to, simultaneously with, or following administration of an antibody of the invention) another therapeutic agent, such as a cytotoxic or radiotoxic agent, which enhances or augments the therapeutic effect of the antibodies.

In other embodiments, the subject can be additionally treated with an agent that modulates, e.g., enhances or inhibits, the expression or activity of Fcγ or Fcγ receptors by, for example, treating the subject with a cytokine. Preferred cytokines for administration during treatment with the multispecific molecule include granulocyte colony-stimulating factor (G-CSF), granulocyte-macrophage colony-stimulating factor (GM-CSF), interferon-γ (IFN-γ), and tumor necrosis factor (TNF).

The compositions (e.g., antibodies, multispecific and bispecific molecules) of the invention can also be used to target cells expressing FcγR or SLAMF6, for example, for labelling such cells. For such use, the binding agent can be linked to a molecule that can be detected. Thus, the invention provides methods for localizing ex vivo or in vitro cells expressing Fc receptors, such as FcγR, or SLAMF6. The detectable label can be, e.g., a radioisotope, a fluorescent compound, an enzyme, or an enzyme co-factor.

In a particular embodiment, the invention provides methods for detecting the presence of the SLAMF6 antigen in a sample, or measuring the amount of the SLAMF6 antigen, comprising contacting the sample, and a control sample, with a monoclonal antibody, or an antigen-binding portion thereof, which specifically binds to SLAMF6, under conditions that allow for formation of a complex between the antibody or portion thereof and SLAMF6. The formation of a complex is then detected, wherein a difference in complex formation between the sample compared to the control sample is indicative of the presence of the SLAMF6 antigen in the sample.

In other embodiments, the invention provides methods for treating an immune-mediated disorder in a subject, e.g., human cancers, small cell lung cancer, non-small cell lung cancer (including squamous carcinomas and adenocarcinomas) skin cancer including melanoma, breast cancer (including TNBC), colorectal cancer, gastric cancer, ovarian cancer, cervical cancer, prostate cancer, kidney cancer, liver cancer including hepatocellular carcinoma, pancreatic cancer, head and neck cancer, nasopharyngeal cancer, oesophageal cancer, bladder cancer and other uroepithelial cancers, stomach cancer, glioma, glioblastoma, testicular, thyroid, bone, gallbladder and bile ducts, uterine, adrenal cancers, sarcomas, GIST, neuroendocrine tumours, and haematological malignancies.

All references cited in this specification, including without limitation all papers, publications, patents, patent applications, presentations, texts, reports, manuscripts, brochures, books, internet postings, journal articles, periodicals, product fact sheets, and the like, one hereby incorporated by reference into this specification in their entireties. The discussion of the references herein is intended to merely summarize the assertions made by their authors and no admission is made that any reference constitutes prior art and Applicants' reserve the right to challenge the accuracy and pertinence of the cited references.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the dependent claims.

The present invention is further illustrated by the following examples which should not be construed as further limiting. The following examples, sequences and figures are provided to aid the understanding of the present invention, the true scope of which is set forth in the appended claims. It is understood that modifications can be made in the procedures set forth without departing from the spirit of the invention.

EXAMPLES

Example 1: Antibody Generation and Screening

Hybridoma Generation

Recombinant ECD protein was used for immunization of mice for generation of mouse Fabs against hu SLAMF6 ECD (SEQ ID NO: 12) at Alere, San Diego.-SLAMF6-hum.ECD Splenocytes from immunized mouse were used to generate a library of fabs using industry standard techniques.

Secondary Screen

Fab supernatants were tested for binding with the SLAMF6 protein expressed on the surface of the Raji cells and activated PBMCs. Supernatants were diluted in 1 in 10 parts with FACS buffer.

Example 2: Structural Characterization of Monoclonal Antibodies to SLAMF6

The cDNA sequences encoding the heavy and light chain variable regions of the monoclonal antibodies were obtained using standard PCR techniques and were sequenced using standard DNA sequencing techniques. The heavy and light chain variable regions of 1B3 selected from the screen can be seen in FIG. 1.

The nucleotide and amino acid sequences of the heavy chain variable region of 1B3 are shown in SEQ ID NO: 3 and 1, respectively.

The nucleotide and amino acid sequences of the light chain variable region of 1B3 are shown in SEQ ID NO: 4 and 2, respectively.

Further analysis of the 1B3 VH sequence using the Kabat system of CDR region determination led to the delineation of the heavy chain CDR1, CDR2 and CDR3 regions as shown in SEQ ID NOs: 5, 6 and 7, respectively. FIG. 1*a* shows 1B3 VH sequences with CDR1, CDR2 and CDR3 boxed.

Further analysis of the 1B3 VL sequence using the Kabat system of CDR region determination led to the delineation of the light chain CDR1, CDR2 and CDR3 regions as shown in SEQ ID NOs: 8, 9 and 10, respectively. FIG. 1*b* shows 1B3 VL sequences with CDR1, CDR2 and CDR3 boxed.

Example 3: Specificity of Fab Supernatants Monoclonal Antibodies to SLAMF6 Determined by Flow Cytometry Analysis 5×10$^6$ Raji cells were placed in each well of a 96 well plate and washed 1× with FACS buffer (DPBS, 2% FBS). The cells were pelleted by spinning for 5 min at 1200 rpm. The pellet was washed 1× with FACS buffer (DPBS, 2% FBS) and again pelleted by spinning for 5 min at 1200 rpm and resuspended in FACS buffer. The test antibody were diluted to 30 nM/l in FACS buffer and increasing amounts as shown in FIG. 4 added to each well which was incubated for 30 min on ice. The cells were then washed 1× with FACS buffer (DPBS, 2% FBS) and pelleted, washed and resuspended in FACS buffer. Secondary goat-anti-mouse antibody was diluted to 1 μg·ml and 100 μl added to each well the plate was incubated for 30 min on ice then washed 1× with FACS buffer (DPBS, 2% FBS). The cells were pelleted and resuspended in 200 ul FACS buffer. Samples were read using the Guava Easycyte Plus HT flow cytometer and results analysed using the Guava Cytosoft software suite.

As can be from FIG. 4 antibody 1B3 exhibits specific dose depended binding to SLAMF6 expressing Raji cells.

Example 4: Ability of Anti-SLAMF6 Antibodies to Activate T Cells and Stimulate IFNγ Production 96-well non-tissue culture plates were coated with 250 ng/ml OKT3 and different concentrations of anti-SLAMF6 antibodies/isotypes at 4° C. overnight. The plates were washed with PBS twice, followed by blocking with R10 media (RPMI with 10% FBS, 1% L-Glutamine, 1% Penicillin/Streptomycin) for 30 min. After blocking, 0.1 million T cells were resuspended into 100 μl R10 medium and added onto the plates (T cells isolated from PBMCs using Miltenyi kit code:130-096-535 as per the manufacturer's instructions). The plates were incubated at 37° C. for 72 hours and the supernatants were collected and diluted for use in an IFNγ ELISA assay.

IFNγ was measured with the IFN-gamma DuoSet ELISA kit (R&D systems Cat. #DY285B) following the manufacturer's instructions.

Results

Figure 5:
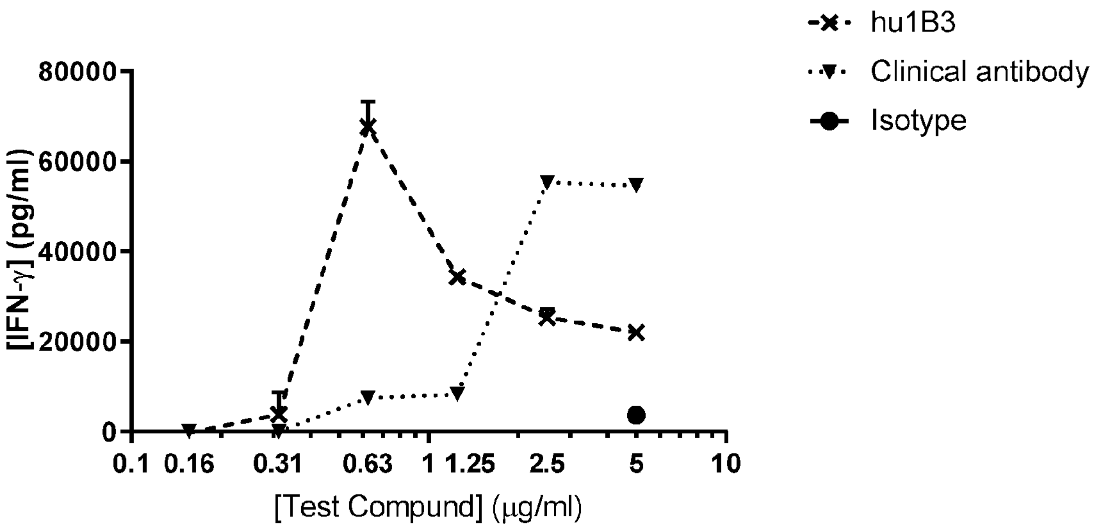
FIG. 5 shows the enhanced ability of antibody Hu_1B3 to mediate IFNγ production upon T cell activation compared to another clinically stage SLAMF6 antibody.

Humanised Antibody Hu_1B3 showed enhanced activity in the OKT3 pre-activated T cells, reflected in increased IFNγ production at a lower antibody concentration, when compared to the Seattle Genetics antibody against SLAMF6 described in WO2017/004330 (FIG. 5). This induction of IFNγ production shows that antibodies directed toward SLAMF6 will have therapeutic effect in patients with inhibited immune systems.

Example 5: Humanisation of Antibody 1B3

The humanization of murine 1B3 monoclonal antibody was performed using CDR-grafting technology. To guide the humanization process and help in the decision to conserve parental murine residues or substitute them with their human germline counterparts a homology molecular model of the Fv of 1B3 murine monoclonal antibody was built. The definition of the CDRs is based on the Kabat nomenclature. The selection of human framework acceptor regions into which 1B3 rat CDR regions are grafted was accomplished by searching the IMGT murine and human V genes database using IgBLAST, developed at NCBI to facilitate analysis of immunoglobulin V region sequences, with 1B3 murine variable region sequences as input. The applied strategy was to use the human germline sequences that are natural human sequences not containing the idiosyncratic somatic mutations found in individual human antibody sequences.

Heavy Chain Design

The amino acid sequence of the VH isolated from the mouse 1B3 hybridoma (CDR regions according to the Kabat numbering scheme are in bold) is shown below.

(SEQ ID NO: 1)

FR1 CDR1 FR2

QVQLKQSGAELVRPGTSVKVSCKASGYAFTNYLIEWVKQRPGQGLEWIG

CDR2 FR3

VINPGSGGTNYNEKFKDKATLTADKSSNTAYMQLSSLTSDDSAVYFCAR

CDR3 FR4

RGWDYEDYWGQGTTLTVSS

Selection of Human Framework Acceptor VH Regions

The selection of human framework acceptor VH regions into which the 1B3 murine CDR regions are grafted was accomplished by searching the IMGT human VH gene database using IgBLAST with the murine VH region amino acid sequence as input. Based on the sequence alignment of the Parental antibody to the human germlines, the closest matching entries were identified. The identification of the optimal human germline as acceptor was based on the following ordered criteria: sequence identity across the framework as defined by Kabat, and identity and/or compatibility of inter-chain interface residues and support loops with the canonical conformations of the Parental CDRs. The human germline IGHV1-2*02 was chosen as the most suitable heavy chain.

Design Using IGHV1-2*02 Human Germline as Framework Acceptor Regions

Humanized Version

Murine CDRs (bold) as defined by the Kabat nomenclature were grafted into IGHV1-2*02 to obtain the hereunder detailed sequence. A number of residues are framework murine residues (outside CDR residues) i.e. conserved from the parental murine 1B3 VH sequence; they have been conserved because they might be structurally important for maintaining the full activity of the antibody.

(SEQ ID NO: 13 aa numbers 1-98)

FR1 CDR1 FR2
QVQLVQSGAEVKKPGASVKVSCKASGYAFTNYLIEWVRQAPGQGLEWIG

CDR2 FR3
VINPGSGGTNYNEKFQGRVTLTADKSISTAYMELSRLRSDDTAVYYCAR 86.7% identity (85 identical residues out of a total of 98 residues in the V gene) of Humanized version (OBT577-12-VHB) with IGHV1-2*02 human germline.

Light Chain Design

The amino acid sequence of the mouse 1B3 VL (CDR regions as defined by the Kabat nomenclature are highlighted) is shown below.

(SEQ ID NO: 2)

FR1 CDR1 FR2
QIVLTQSPALMSTSPGEKVTMTCSASSSVSYIYWFQQKPGSSPKPWIYR

CDR2 FR3 CDR3
TSNLASGVPARFSGSGSGTSYSLTISSMEAEDAATYYCQQWDNNPYTFG

FR4
GGTKLEIK

Selection of Human Framework Acceptor VL Regions

The selection of human framework acceptor VL regions into which the 1B3 VL murine CDR regions are grafted was accomplished by searching the IMGT human VL genes database using IgBLAST with the murine VL region amino acid sequence as input. Based on the sequence alignment of the Parental antibody to the human germlines, the closest matching entries were identified. The identification of the optimal human germline as acceptor was based on the following ordered criteria: sequence identity across the framework as defined by Kabat, and identity and/or compatibility of inter-chain interface residues and support loops with the canonical conformations of the Parental CDRs. From this analysis, human germline, IGKV1-33*01, appeared to be the best choice as human framework acceptor regions. Thus, this human germline was used for the design of the humanized versions.

Design Using IGKV1-33*01 Human Germline as Framework Acceptor Regions

Humanized Version

Murine CDRs as defined by the Kabat numbering were grafted into IGKV1-33*01 to obtain the hereunder detailed sequence. A number of residues structurally important for maintaining the full activity of the antibody have been retained. This gave a humanised version with 86.3% identity (82 amino acid residues out of 95).

(SEQ ID NO: 14 aa numbers 1-94)

FR1 CDR1 FR2
DIQLTQSPSSLSASVGDRVTITCQASQDVSYIYWYQQKPGKAPKPWIY

CDR2 FR3 CDR3
RTSNLATGVPSRFSGSGSGTDYTFTISSLQPEDIATYYCQQWDNNP

86.3% identity (82/95) of humanized version with IGKV1-33*01 human germline

Example 6 ELISPOT with Tumor Infiltrating Lymphocytes

Primary tumor-derived tumor infiltrating lymphocytes (TILs) from NSCLC (FIG. 6), Breast cancer (FIG. 7) or CRC (FIG. 8) tumors were stimulated for 96 h with murine 1B3 or pembrolizumab at 10 μg/ml and OKT3 diluted to 1 μg/ml in complete IMDM culture media. After stimulation TILs were harvested, counted and plated on IFNγ ELISPOT plate (Mabtech) at 100 000 cells/well. The plate was incubated at 37° C. for 24 hours and subsequently developed according to the manufacturer's instructions. The number of spots was read using ImmunoSpot® Series 5 ELISPOT analyser the data was analysed using GraphPad Prism software.

Figure 6:
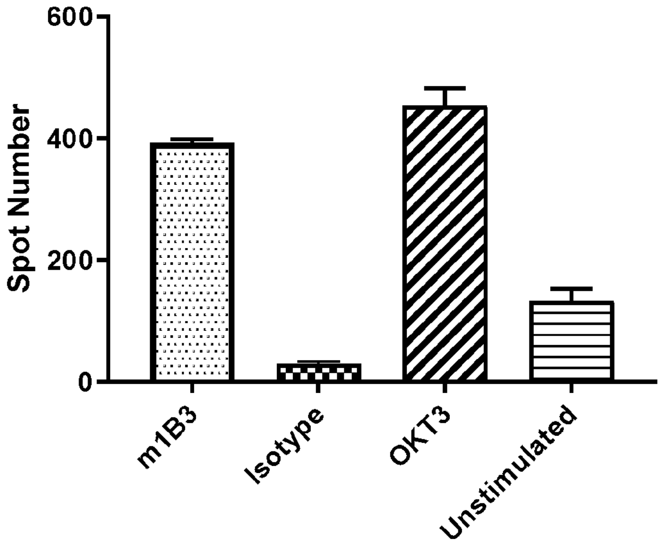
FIG. 6 shows that antibody 1B3 can induce tumor infiltrating lymphocytes (TILs) isolated from primary NSCLC tumor samples to produce interferon gamma in ex vivo assays.

FIG. 6 shows that antibody 1B3 activates a NSCLC derived TILs reflecting a significantly higher IFNγ production than the isotype antibody.

Figure 7:
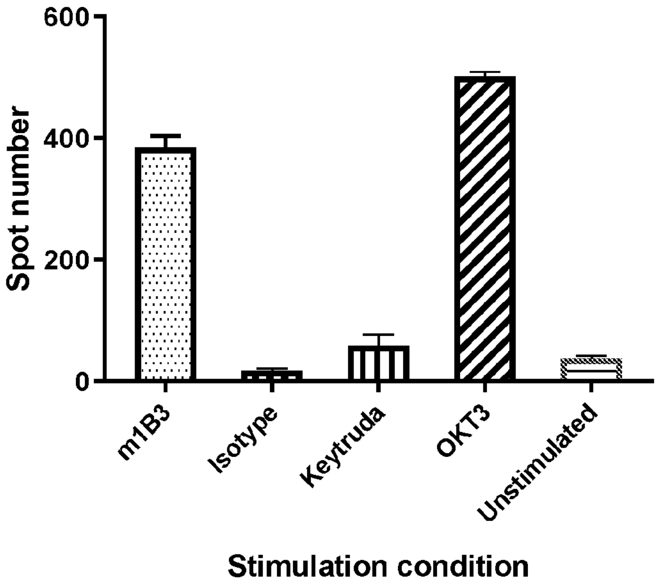
FIG. 7 shows that antibody 1B3 can induce TILs isolated from primary breast cancer samples to produce interferon gamma in ex vivo assays. This assay shows that antibody 1B3 has enhanced activity when compared to pembrolizumab.

FIG. 7 shows that antibody 1B3 activates a significantly greater number of breast cancer derived TILs to produce IFNγ than pembrolizumab.

Figure 8:
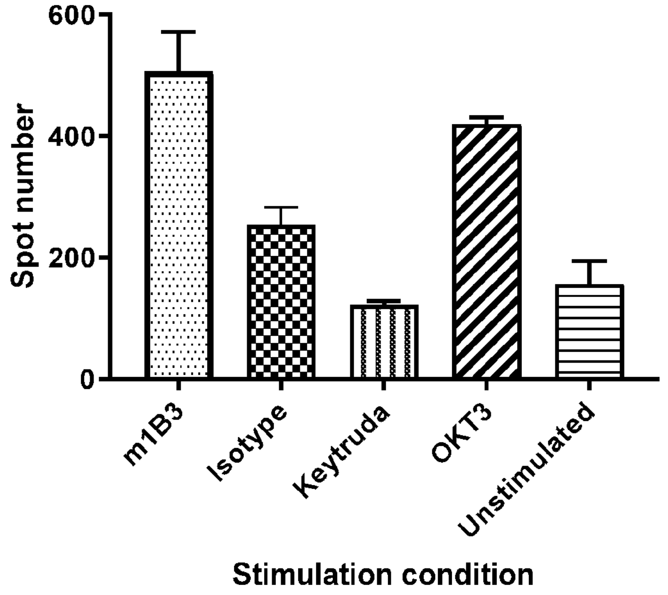
FIG. 8 shows that antibody 1B3 can induce TILs isolated from primary colorectal cancer samples to produce interferon gamma in ex vivo assays. This assay shows that antibody 1B3 has enhanced activity when compared to pembrolizumab.

FIG. 8 shows that antibody 1B3 activates a significantly greater number of colorectal cancer derived TILs to produce IFNγ than pembrolizumab.

Example 7 Binding Affinity of the Humanised 1B3 Antibody

Binding affinity experiments were performed on Biacore T-200 at 25° C. Flow cells 2, 3 and 4 of the CM5 chip were coated with maximum amounts 500 RU of goat anti-human IgG. Test Ab were captured on flow cells 2, 3 and 4. Flow cell 1 was kept blank and used for reference subtraction. Antigen was flowed over the chip. Binding of antigen to the antibodies was monitored in real time. From the observed $k_{on}$ and $k_{off}$, KD was determined.

TABLE 2

| Sample | $K_D$ (M) | $K_A$ (1/M) | $k_{on}$ (1/Ms) | $K_{off}$ (1/s) | Full $X^2$ |
|---|---|---|---|---|---|
| 1B3 | $1.72 \times 10^{-9}$ | $5.8 \times 10^{8}$ | $5.41 \times 10^{5}$ | $9.32 \times 10^{-4}$ | 0.227 |

Example 8 In Vitro Proliferation Assay Using Anti SLAMF6 Antibody 1B3

Methods.

Non-tissue culture-treated 96-well plates (BD Falcon, USA) were coated with anti-human CD3 (eBioscience, USA) antibody at 250 ng/ml alone or in combination with the humanised anti-SLAMF6 antibody (Hu_1B3), or isotype control antibodies at concentrations 0. 0.2, 0.4, 0.6, 0.9 and 1.2 ug/ml) and incubated overnight at 4° C. The following day plates were washed and blocked with AIM V media. T cells isolated from PBMCs generated from a healthy donor were stained with cell proliferation dye eFluor™ 670 (eBioscience, USA), washed and seeded onto the antibody-coated plates (100,000 cells per well in 100 μl) in AIM V (Thermofisher Scientific, USA) media containing FCS, penicillin-streptomycin, and cultured for 72 hours at 37° C. in tissue culture incubator. On day 3 Cells were collected and stained with FITC labeled anti-human CD8, Brilliant Violet 711™ labeled anti-human CD4, PE labeled anti-human CD69 (Biolegend, USA), and fixable viability dye eFluor™ 506 (eBioscience, USA). Samples were analyzed on an attune N×T flow cytometer (Thermofisher Scientific, USA) and data analyzed using FlowJo software (TreeStar, USA).

Figure 9:
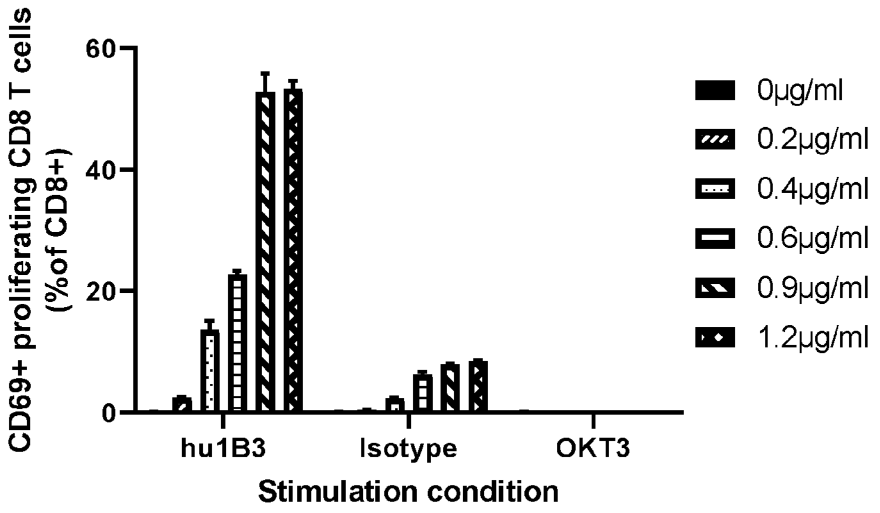
FIG. 9 shows that activation of SLAMF6 present on isolated T cells using antibody Hu_1B3 induces proliferation of CD8+ T cells.

FIG. 9 shows that stimulation of SLAMF6 present on the isolated T cells using an the anti-SLAMF6 antibody in the presence of CD3 results in significantly increased T-cell proliferation when compared to isotype or CD3 alone.

Example 9 One-Way Mixed Lymphocyte Reaction (MLR) with Allogeneic PBMCs Using Anti-SLAMF6 Antibody Hu_1B3

Method:

Isolated T cells from one donor (Donor 1) were resuspended in RPMI 1640 medium with 10% supplemented bovine serum and 2 mM L-glutamine (culture medium). Cryopreserved PBMCs from a second donor (Donor 2) were treated with 50 ug/ml mitomycin C at a density of 2E6 cells/ml in culture medium. The cells were treated for ninety minutes at 37° C. before removal of mitomcyin C by washing with culture medium. 100,000 cells from Donor 1 were then combined with 100,000 mitomycin C-treated cells from Donor 2 in a 96 well, U-bottom plate. The combined cells were treated with various concentrations of humanized antibody Hu_1B3 and controls in solution and cultured for six days in a total volume of 100 ul culture medium/well. Isotypes were used as negative controls as well as an anti-CD137 mAb, included for comparison.

Culture supernatants were harvested on day six and assayed for the concentration of IFN-γ by ELISA (R&D Systems: DY285B), according to the manufacturer's instructions.

Figure 10:
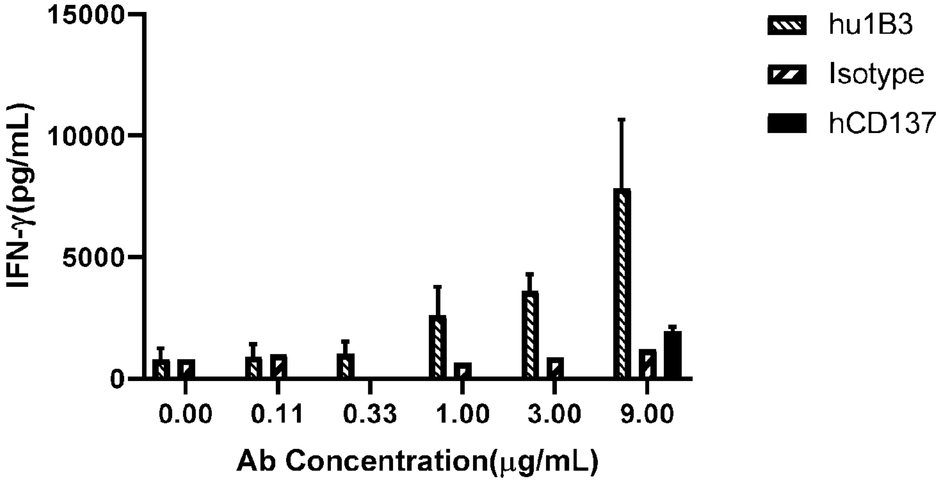
FIG. 10 is an MLR assay and shows that antibody Hu_1B3 can induce DC mediated T cell activation as highlighted by increase in IFNy release.

FIG. 10 shows that anti-SLAMF6 antibody Hu_1B3 shows a dose related increase in cytokine release indicating that the T-cells are being activated by the presence of the antibody. It also shows that activation of SLAMF6 results in higher cytokine release from isolated T cells than activation via CD137.

Example 10 SLAMF6 Mediated Granzyme B and Perforin Release from T Cells

PBMC Isolation

As the first step in T cell isolation, PBMCs are isolated from the buffy coat (Leucopak from Stanford Blood Center). Blood is diluted in PBS at 1:4 ratio (10 ml blood+30 ml PBS) and 30 ml of the diluted blood is carefully laid over 15 ml of Ficoll-Hypaque (GE-Healthcare cat. No. 17-1440-03). The tubes are centrifuged at 400g (1400 rpm) in a sorvall centrifuge for 30 min at RT with brakes off. Monocytes are separated by density gradient. Around 10 ml of the cellular white fraction from all tubes are pooled into a single 50 ml tube, washed and counted using Cellometer auto 2000. PBMC generated from buffy coats are used for T cell isolation.

T Cell Isolation

Pan T cells isolation from the PBMCs is a negative selection process where except for CD4 and CD8 T cells all the remaining immune cell subsets are labeled with Biotin conjugated antibodies and captured by streptavidin-coated microbeads in a high magnetic field. PBMCs isolated from the buffy coats are washed and resuspended in FACS sorting buffer (0.1% BSA in PBS) at a concentration of 2.5e7 cells/mL and Pan T Cell Biotin-Antibody Cocktail is added to the cells, the antibody cell suspension is mixed using a 1 ml pipette and incubated on ice for 5 minutes. Pan T Cell MicroBead isolation cocktail is added to the mixture and incubated on ice for another 10 minutes. MACS separation technique is used for isolating untouched T cells. The biotin-labeled-microbead mixture of PBMCs is run over an LS column (Miltneyi Biotec, Cat #130-042-401) in high magnetic field MACS separator and the flow-through depleted of non T cells is collected, washed once with FACS sorting buffer and resuspended in AIMV complete media with 5% FBS.

Granzyme B ELISA

For the Granzyme B functional assay, non-tissue culture treated 96 well plates are coated with the human Hu_1B3 or the isotype control antibodies in combination with 250 ng/ml of anti-human CD3 (OKT3 clone)(Thermofisher Scientific Cat #16-0031-85). Each of the test antibodies are coated starting at 4.2 μg/ml with 2:3 dilutions for 10 point titration in triplicate in 100 μl of PBS. The plates are sealed and incubated overnight at 4° C. On the day of the granzyme B functional assay setup, the plates are washed and blocked with AIMV complete media with 5% FCS for 20 minutes to reduce non-specific binding.

Figure 11:
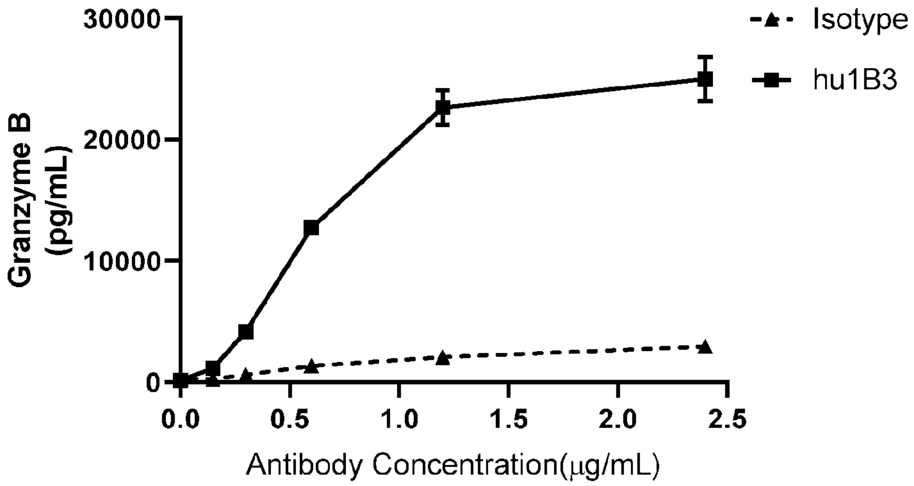
FIG. 11 shows that anti-SLAMF6 antibody Hu_1B3 can induce activated T cells to produce Granzyme B in a dose dependent manner.

The granzyme B immunoassay is setup using the Human Granzyme B DuoSet ELISA kit from R&D systems (Cat #DY2906-05). Nunc-immunoassay plates are coated with granzyme B capture antibody diluted at 1:60 in PBS and the plates are incubated overnight at 4° C. The following day the plates are washed with ELISA wash buffer (PBS+0.05% tween 20) and blocked with 1% BSA in PBS. After blocking the plate 100 μl of samples diluted at 1:60 in dilution buffer, and standards are added to the respective wells and incubated overnight at 4° C. The following day the plates are developed, and OD values captured on a VersaMax tunable microplate reader. The Granzyme B release is quantified and plotted using Graphpad Prism 8 software Conclusion Granzyme mediated apoptosis is one of the primary mechanism employed by cytotoxic lymphocytes to eliminate transformed cells. The data shows that antibody Hu_1B3 is able to induce cytotoxic function which is critical for tumour suppression. Antibody Hu_1B3 induces a dose dependent increase in granzyme B from the activated T cells (FIG. 11) with an $EC_{50}$ at 0.51 μg/ml.

Perforin Intracellular Assay

Perforin intracellular quantification assay setup non-tissue culture treated 96 well plates are coated with the human Hu_1B3 or the isotype control antibodies in combination with 250 ng/ml of anti-human CD3 (OKT3 clone)(Thermofisher Scientific Cat #16-0031-85). Each of the test antibodies are coated starting at 4.2 μg/ml with 2:3 dilutions for 10 point titration in triplicate in 100 μl of PBS. The plates are sealed and incubated overnight at 4° C. On the day of the granzyme B functional assay setup, the plates are washed and blocked with AIMV complete media with 5% FCS for 20 minutes to reduce non-specific binding. For this assay 200,000 pan T cells are added per well in 100 μl of AIMV culture media with 5% FBS and cultured for 3 days at 37° C. in tissue culture incubator. On the day of assay, the protein transport inhibitor cocktail (Thermofisher Scientific, Cat #00-4980-93) is added to all wells and cultured for 4 hours to prevent perforin transport to the extracellular space. The cells are collected and stained for T cell surface markers CD3, CD4, and CD8 followed by intracellular perforin staining using FIX & PERM™ cell permeabilization kit (Thermofisher Scientific, Cat #GAS-004). The cells are analyzed on Attune N×T FACS analyser (Thermofisher Scientific, MD) and the data is analyzed with FlowJo software (BD Biosciences, San Jose).

Conclusion

Figure 12:
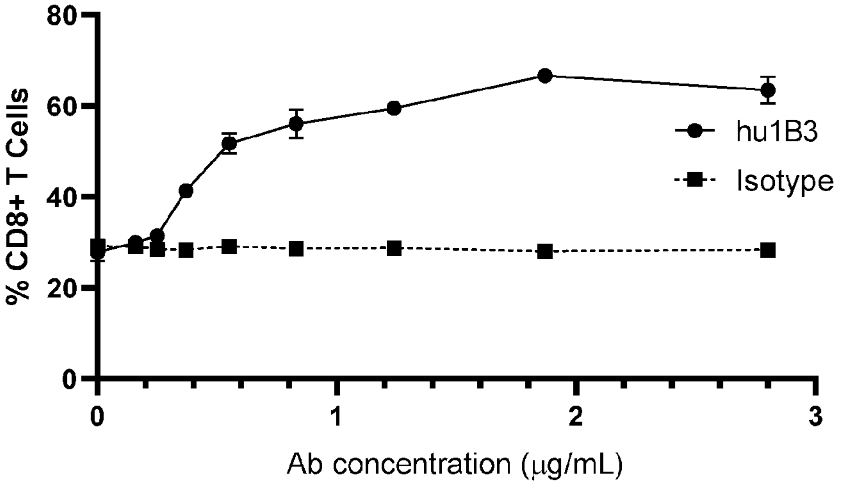
FIG. 12 shows that antibody Hu_1B3 upregulates perforin expression on CD8+ T cells in a dose-dependent manner.

Perforin mediated necrosis is another major mechanism of killing induced by cytotoxic T lymphocytes and Hu_1B3 enhances upregulation of perforin in CD8+ T cells in a dose-dependent manner (FIG. 12) with an $EC_{50}$ at 0.44 μg/ml Example 11 Competitive Binding Assay to Assess the Binding Epitope of Antibody 1B3

Cryopreserved human PBMCs were thawed and washed once by suspension in FACS buffer (DPBS with 2% FCS) followed by centrifugation for 5 minutes at 1200 rpm to pellet cells and discarding of supernatant (same method used for subsequent washes). The cells were dispensed into a 96-well assay plate at 100,000 cells per well in FACS buffer before being washed once more. Cells were then blocked with SLAMF6 ECD-mIgG2a Fc fusion protein at 100 nM or 300 nM for 1 hr for SLAMF6 receptor blocking in 100 μl FACS buffer on ice for 1 hour before being washed. Humanized Hu_1B3 antibody or human IgG1 Isotype control at top concentration of 10 nM and a titration by serial dilution of 1 in 3, was then added to the blocked PBMCs and the cells were incubated for 1 hr on ice before being washed twice. The secondary antibody, goat anti-human-IgG-RPE (Southern Biotech, Ref: 2040-05) at a concentration of 1 μg/mL in FACS buffer, was then applied to the treated cells for 30 minutes on ice. One previously untreated well containing cells was also stained with secondary antibody and another was left unstained to act as controls for secondary antibody binding. After this final incubation, cells were again washed twice, and the final cell pellets were re-suspended in FACS buffer. Mean fluorescence intensity for the secondary antibody was determined for each sample using an Attune N×T Flow Cytometer (ThermoFischer Scientific) in a 96-well plate format according to industry standard protocols, and the raw data was analyzed using FlowJo analysis software.

Figure 13:
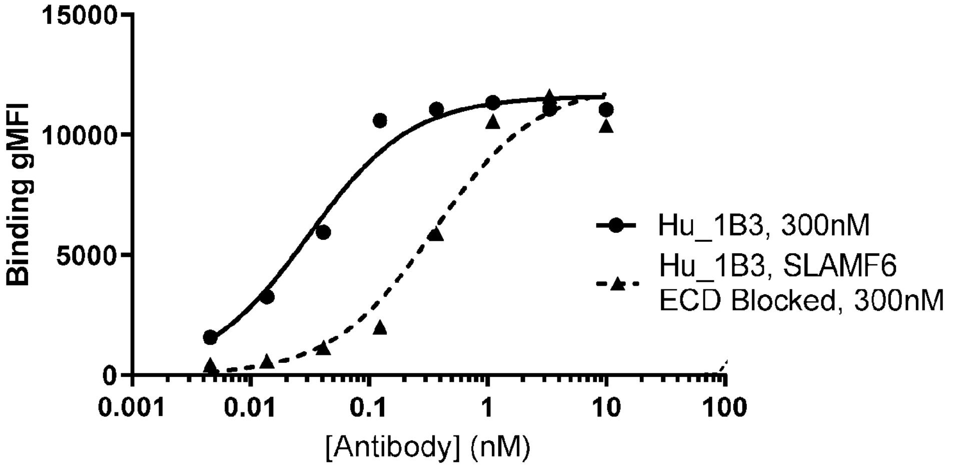
FIG. 13 shows that Hu_1B3 antibody is blocked from binding to the receptor on the surface of PBMCs in the presence of human SLAMF6 ECD-mIgG2a Fc fusion protein.

As seen in FIG. 13, Hu_1B3 antibody is blocked from binding to the receptor on the surface of PBMCs in the presence of human SLAMF6 ECD-mIgG2a Fc fusion protein, indicating that Hu_1B3 binds competitively with human SLAMF6 ECD. It may therefore be considered that Hu_1B3 binds to the homodimerization epitope of SLAMF6, and augments cytotoxic T cell function through the SAP-mediated activating pathway, functioning as an agonist antibody.

Example 12 Internalization of Hu_1B3 Antibody

RAJI, human Burkitt's lymphoma cells (Cat No CCL-86, American Type Culture Collection [ATCC], Manassas VA) were grown in RPMI-1640 medium (Cellgro, Cat No 10-041-CM, Mediatech, Manassas VA) supplemented with 10% fetal bovine serum (HyClone* Cosmic Calf Serum, Cat No SH30087-03, Thermo Scientific, Waltham, MA) and 1% sodium pyruvate (Cellgro, Cat. #25-000-CI) using industry standard aseptic techniques RAJI cells were plated at a density of 5×105 cells per well in 24-well cell glass bottom culture plates and were allowed to proliferate for 48 hours at 37° C. in growth media. Wells were prepared for the following samples: Secondary antibody only control, human IgG isotype control, antibody Hu_1B3, clinical anti-SLAMF6 antibody from Seattle genetics (positive control) at 0h, 0.5h, 1 h, 2h, 4 h and 24h. Secondary only control well and no antibody control well were used as fluorescent controls.

All antibody incubations and wash steps were subsequently performed on ice with ice-cold reagents. The culture media was aspirated from the wells and were washed twice with IF buffer (Dulbecco's phosphate-buffered saline (DPBS, Thermo Scientific, Waltham VA, Cat. #SH30028-03)+2% FBS). The primary antibody (purified OBT humanized Hu_1B3; Isotype or positive control antibody (Seattle Genetics), was diluted to 2 ug/mL in IF buffer and 200 μl were applied to the appropriate wells for 15 minutes. The same volume of IF buffer alone was added to the well designated for the secondary antibody control. Secondary antibody (goat anti-human IgG—Alexa Fluor® 488 (green-fluorescent dye), Invitrogen Cat. #A11013) was diluted to a concentration of 2 ug/mL in IF buffer and also added to the primary incubation for 15 minutes.

Following primary and secondary antibody labeling, human IgG isotype control, secondary antibody only control, and Test and positive control at 0 minutes samples were processed. The cells were washed twice with IF buffer and placed into a second 24-well plate containing 4% paraformaldehyde (4% diluted by half in DPBS, Cat No 19943, Affymetrix, Santa Clara, CA) on ice in order to stop internalization and fix the cells.

The remaining cells were washed twice with IF buffer and 1 mL of warmed growth media was added to each well before placing in a 37° C. incubator. At 0h, 0.5h, 1 h, 2h, 4 h, 24h cells were fixed in paraformaldehyde on ice as described for the control samples.

All of the cells remained in fixative on ice for at least 15 minutes. The cells were washed with IF buffer and coverslips were added to each well along with 2-3 drops of Prolong Gold Anti-Fade reagent plus DAPI (Cat No P-36931, Invitrogen, Grand Island, NY) as a nuclear counter stain. Cell images were acquired using a Leica Microscope (Leica DMI600B), Leica monochrome camera (Leica DFC350FX), filter sets for DAPI and Alexa Fluor® 488 (green-fluorescent dye) and 63× oil immersion lens. Images were saved in TIFF format and analyzed using ImageJ.

Figure 14:
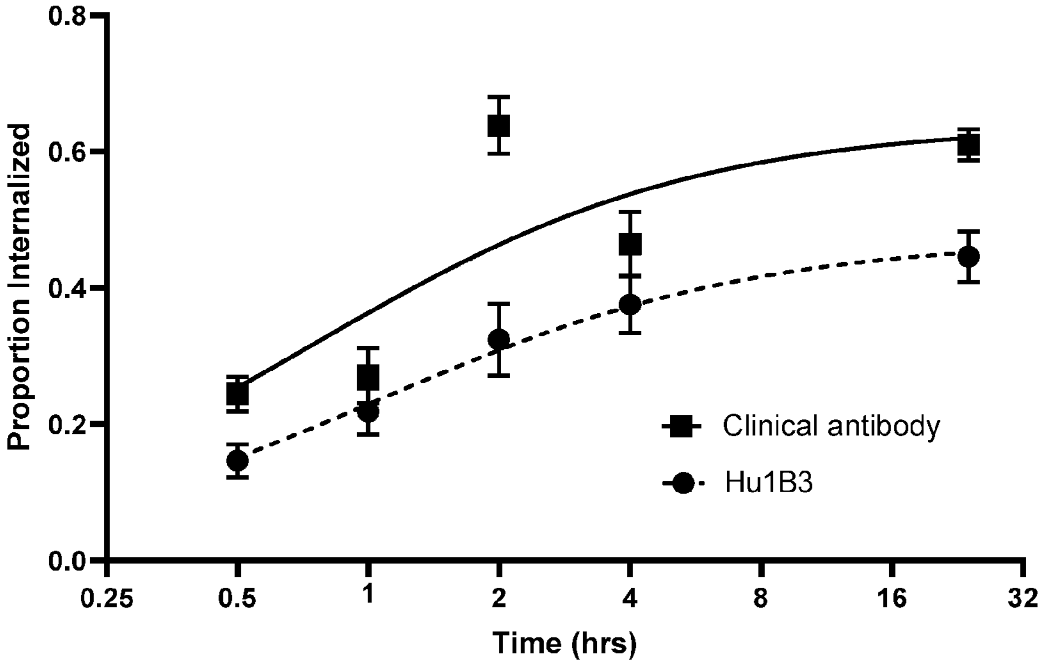
FIG. 14 shows that humanized antibody Hu_1B3 internalises into SLAMF6 expressing cells significantly less than the anti SLAMF6 antibody produced by Seattle Genetics.

FIG. 14 shows that humanized antibody Hu_1B3 internalises into SLAMF6 expressing cells significantly less than the clinical Seattle Genetics antibody. This indicates that upon binding to antibody Hu_1B3 the receptor remains on the surface of the cell for longer and therefore will induce a more durable response in T cells and therefore will be a more effective agonist.

Example 13 Cytotoxicity Assays

SKBr3 HCT116 and MDA-MB-231 were purchased from ATCC. Cell lines were maintained as directed by the manufacturer (ATCC) using standard aseptic techniques. Cell culture medium consisted of RPMI-1640 with 2 mM L-Glutamine and 25 mM HEPES (Corning), 1% Penicillin/Streptomycin (Sigma-Aldrich), and 10% heat-inactivated FCS (HyClone). Cell lines were maintained in the exponential phase and grown in a 37° C. incubator containing 5% $CO_2$. SKBr3 is a breast cancer cell line that expresses a high copy number of Her2 (~$5\times10^6$ copies/cell). HCT116 is a colorectal cancer cell line that expresses a low copy number of Her2. MDA-MB-231 is a breast cancer cell line that express a low copy number of Her2.

Target and effector (PBMC) cells were prepared under the following conditions. The day prior to the assay, target cells were washed with PBS, incubated with 0.25% Trypsin, and resuspended in cell culture media. Viability and cell concentration were measured by the dye-exclusion method. Target cells were plated at 10,000 cells/well in 96-well tissue culture treated plates. The cells were grown overnight in a 37° C. incubator with 5% $Co_2$. The day prior to the assay, frozen PBMC's were thawed in a 37° C. water bath, washed with cell culture media, and grown overnight in 37° C.

incubator with 5% $CO_2$. The following day, the viability and cell concentration were measured by dye-exclusion. PBMC's were added to the target cells at an E:T ratio of 10:1. 10,000 target cells were mixed with 100,000 effector cells.

The bispecific antibody, Cris7-Her2, was used in the cytotoxicity assay. The antibody detects both Her2 and CD3E. Cris7-Her2 Bispecific antibody was diluted to 100 ng/ml, and then serially diluted 3-fold to 0.0012 ng/ml. In addition, Cris7-Her2 plus agonist antibody was tested. The combination of Cris7-Her2 Bispecific antibody plus agonist antibody was included to observe enhanced cytotoxicity by the agonist antibody. Urelumab, an antibody directed against 4-1BB, was used as a positive control. Isotype was used as a negative control. Hu_1B3 was the test article. Urelumab, Isotype, and Hu_1B3 were used at a final concentration of 2.5 ug/ml. All samples were run in triplicate. Controls included target cells alone or target cells plus effector cells. Additional controls included target cells and effector cells plus Hu_1B3 or target cells and effector cells plus isotype control. Cytotoxicity assays were incubated for 48-96 hours depending on the cell line. Following incubation, the viability of the target cells was measured. Viability is based on the quantitation of ATP, which signals the presence of metabolically active cells. The assay is luminescence-based, and Cell Titer-Glo® (Promega, Madison, WI) was the reagent used to measure live cells. For assay conditions, the manufacturer's instructions were followed, and all steps were done at room temperature. Briefly, the 96-well plate and Cell Titer-Glo® reagent were equilibrated to room temperature for 30 minutes. After 30 minutes, cell culture media was removed, and target cells were washed with 200 ul of PBS; the wash step was repeated one more time. Next, 100 ul of Cell Titer-Glo® reagent was added to all wells.

The plate was placed on an orbital shaker and mixed at 250 rpm for 2 minutes to induce cell lysis. The plate was removed from the orbital shaker and incubated for 10 minutes in the dark to stabilize the luminescent signal. After 10 minutes, the samples were transferred to opaque-walled 96-well plates and the luminescence was recorded.

Figure 15:
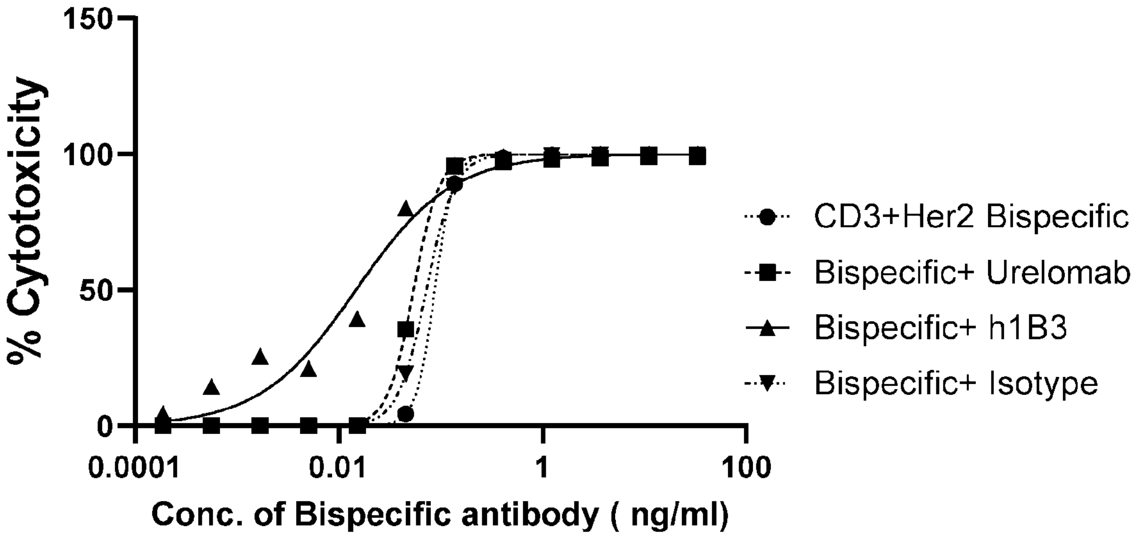
FIGS. 15 and 16 show the addition of Hu_1B3 enhances lymphocyte cytotoxicity against SKBR-3 cells when used with a anti her2 antiCD3 Bispecific antibody.

The viability of the target cells was proportional to the luminescent signal generated. All samples were done in triplicate and the mean was calculated for each assay condition. The percent cytotoxicity of the sample was normalized to the control; the control was the viability of the target cells in the presence of effector cells (Target+Effector). To calculate viability, the luminescent signal of the sample was divided by the luminescent signal of the control. Cytotoxicity was calculated based on the percentage of non-viable cells that remained. As seen in the FIG. 15, for SKBr3 cells, the bispecific antibody alone or the bispecific antibody plus isotype control have an effective cytotoxicity at higher concentrations from 0.8 to 100 ng/ml. The addition of Urelumab shifts the cytotoxicity curve slightly to the left, but not more than 5%. However, the addition of 2.5 ug/ml of Hu_1B3 enhanced the cytotoxicity of SKBR-3 cells by 10 to 40%.

Figure 16:
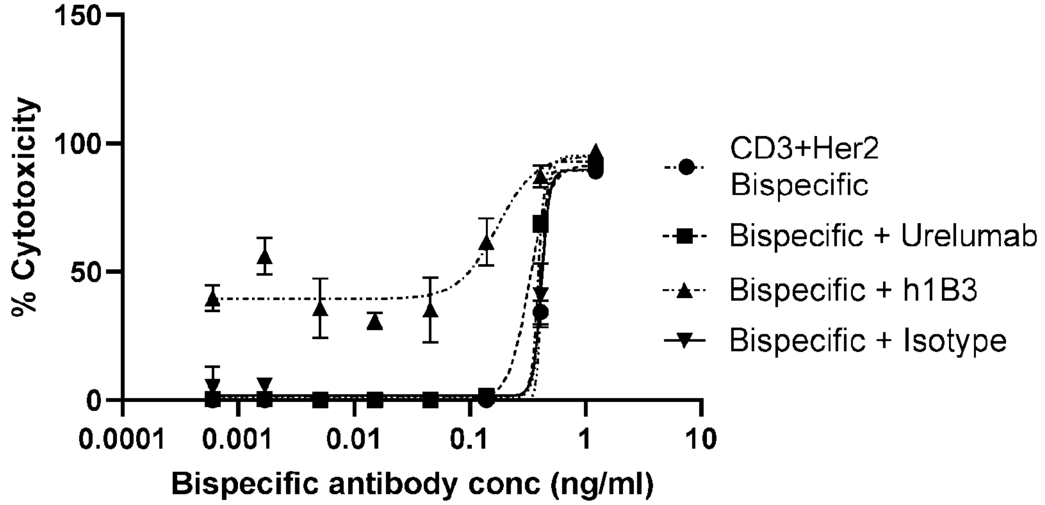

FIG. 16 shows that in a second PBMC donor a similar result is seen.

Figure 17:
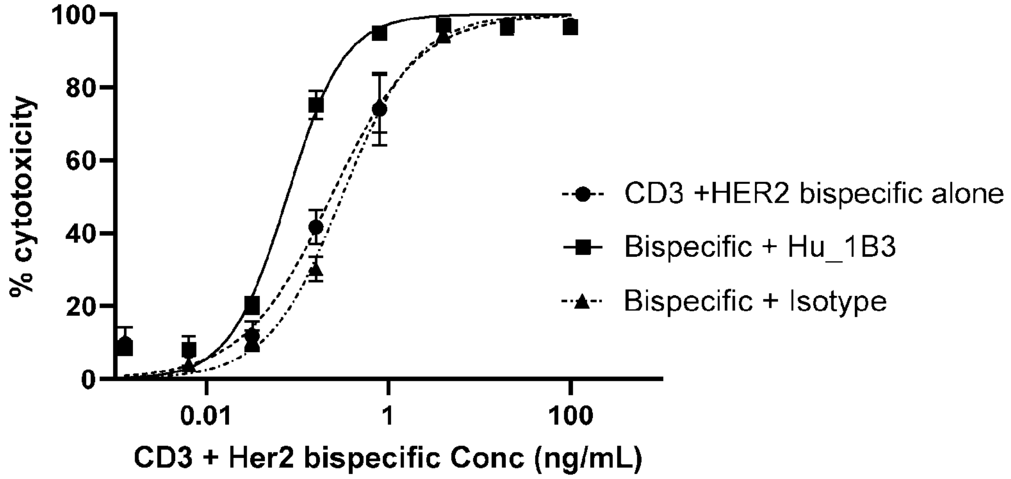
FIG. 17 shows the addition of Hu_1B3 enhances lymphocyte cytotoxicity against HCT116 cells when used with a anti her2 antiCD3 bispecific antibody

FIG. 17 shows enhanced cytotoxicity by Hu_1B3 against HCT116 cells. HCT116 cells, a colon carcinoma cell line, expresses low levels of Her2 on the cell surface. The cytotoxicity assay was done using HCT116 cells, along with PBMC's, and a T-cell engaging bispecific antibody, Cris7-Her2. As described above Hu_1B3, was added to the assay to determine if it enhances the function of T cells or NK cells, which are present in PBMC's; T cells and NK cells both express the co-activating receptor, SLAMF6. The data shows dose-dependent cytotoxicity by the T-cell engaging bispecific antibody, Cris7-Her2, at the various concentrations tested. More importantly, the data shows when Hu_1B3 was added, an increase in cytotoxicity was observed. The EC50 for Cris7-Her2 bispecific alone or Bispecific antibody+Isotype control is approximately 0.25 ng/mL, whereas, the EC50 for Bispecific antibody+Hu_1B3 is approximately 0.07 ng/ml. This represents an approximately 3.6-fold increase in cytotoxicity.

Figure 18:
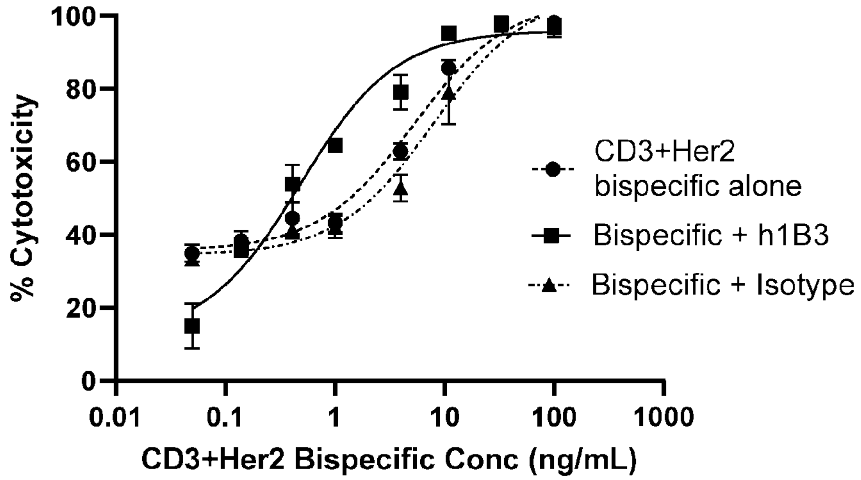
FIG. 18 shows the addition of Hu_1B3 enhances lymphocyte cytotoxicity against MDA-MB-231 cells when used with a anti her2 antiCD3 bispecific antibody.

FIG. 18 shows enhanced cytotoxicity by Hu_1B3 against MDA-MB-231 cells. MDA-MB-231 cells, a breast cancer cell line, expresses low levels of Her2 on the cell surface. A cytotoxicity assay was done using MDA-MB-231 cells, along with PBMC's, and a T-cell engaging bispecific antibody, Cris7-Her2 as described above. Again, Hu_1B3 enhances the cytotoxicity of Cris7-Her2 Bispecific, at the various concentrations tested. Specifically, a 40% increase in cytotoxicity was observed at 1 ng/mL of Cris7 compared to the isotype control.

Figure 19:
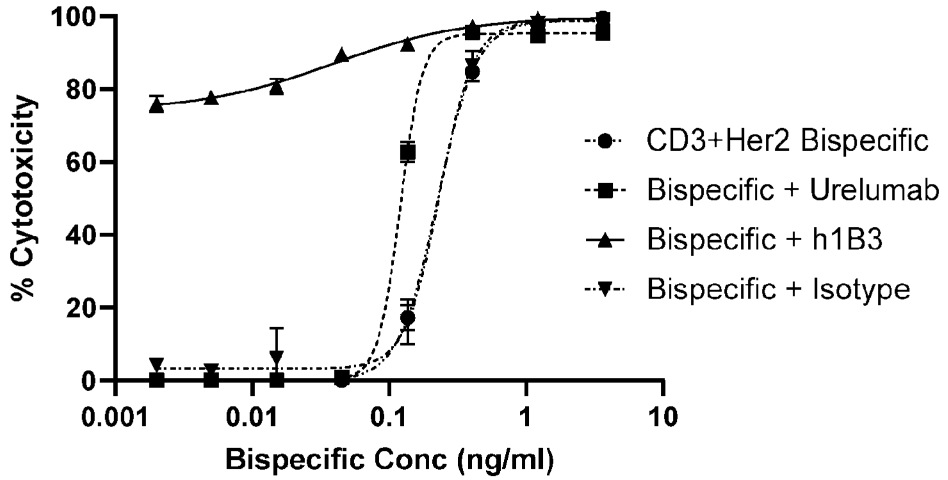
FIG. 19 shows that after activation of lymphocytes for 96 hours with various antibodies, antibody HU_1B3 results in the death of significantly more SKBR-3 cells than either Urelumab (anti-CD137) or isotype.

FIG. 19 shows that after incubation for 96 hours, the combination of the bispecific and Hu_1B3 showed high levels of killing of SKBR-3 cells even the lowest levels of bispecific antibody concentration. Whereas, at these levels either the bispecific alone or the bispecific in combination with Urelumab or the isotype control resulted in very low levels or no cell kill suggesting that Hu_1B3 provides strong activation of lymphocytes.

Figure 20:
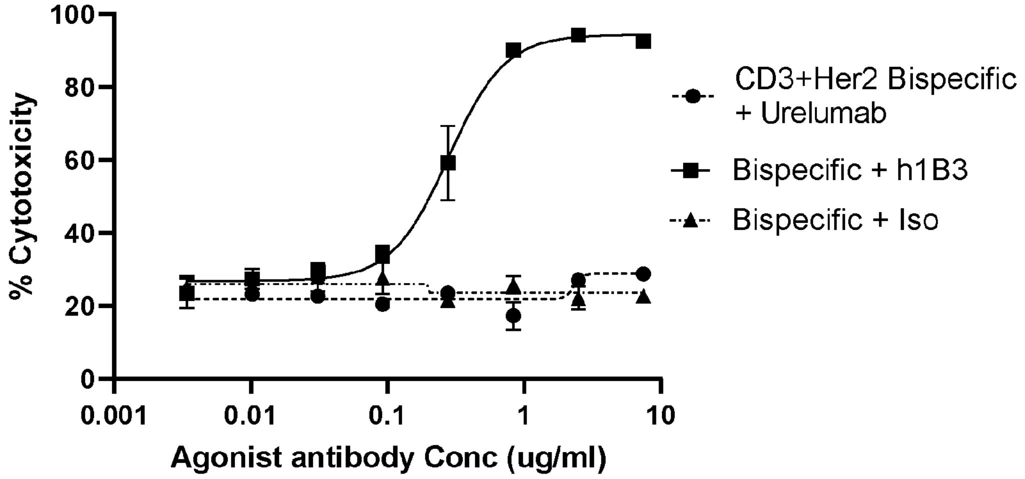
FIG. 20 shows the addition of Hu_1B3 enhances lymphocyte cytotoxicity against SKBR-3 cells in a dose dependent manner when used along with fixed concentration of antiHer2/anti CD3 bispecific antibody.
Figure 17A:
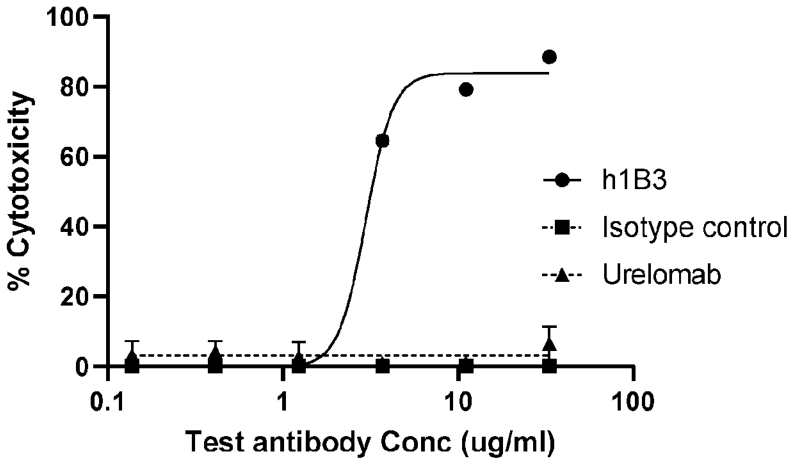
Figure 17B:
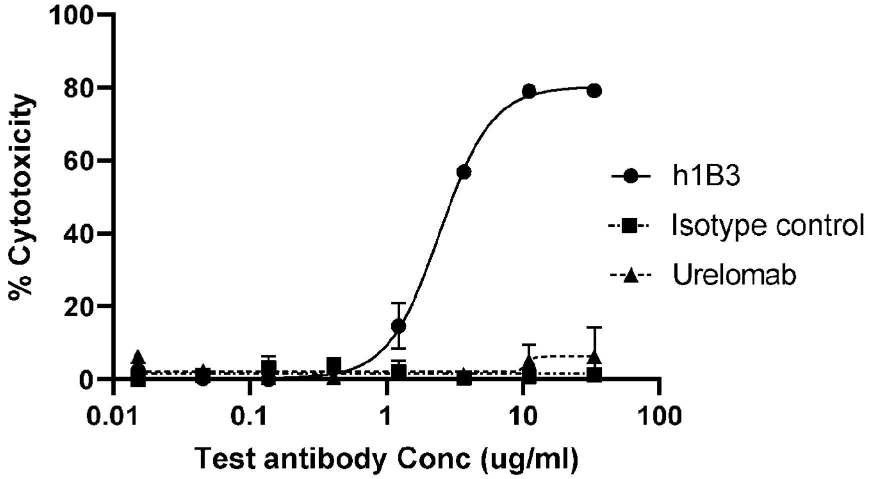

FIG. 20 shows that in the cytotoxicity assays described above Under test conditions in which the bispecific Cris 7-Her2 antibody is maintained at a constant level (0.0457 ng/ml) and the concentration of the test antibody is titrated by ⅓ dilution in the concentration ranges from 7.5 ug/ml to 0.0034 ug/ml. A dose dependent killing of SKBR-3 cells was observed as compared to Urelumab or the isotype control, further indicating the ability of Hu_1B3 to activate cytotoxic lymphocytes.

Example 14 Cytotoxicity Assay in the Absence of Cris7 Bispecific

Another cytotoxicity assay was set as described above, however bispecific antibody was not used. Only Hu_1B3, Isotype control and Urelumab were used to test the cytotoxicity of single agents with SKBR-3. Concentration range used in the assay was from 33 ug/ml to 0.13 ug/ml with ⅓ dilutions with one donor. Test antibody was further diluted to 0.0152 ug/ml for the second donor (FIG. 21*b*).

FIGS. 21*a* and 21*b* show that in the absence of the CD3-Her2 bispecific antibody Hu_1B3 is capable of activating lymphocytes to induce cell killing of SKBR-3 cells. This is in contrast to Urelumab or isotype control where very little cell killing is seen.

Sequence List

| SEQ ID | Description | Sequence |
|---|---|---|
| 1 | 1B3_VH_aa | QVQLKQSGAE LVRPGTSVKV SCKASGYAFT NYLIEWVKQR PGQGLEWIGV INPGSGGTNY NEKFKDKATL TADKSSNTAY MQLSSLTSDD SAVYFCARRG WDYFDYWGQG TTLTVSS |
| 2 | 1B3_VL_aa | QIVLTQSPAL MSTSPGEKVT MTCSASSSVS YIYWFQQKPG SSPKPWIYRT SNLASGVPAR FSGSGSGTSY SLTISSMEAE DAATYYCQQW DNNPYTFGGG TKLEIK |
| 3 | 1B3_VH_nt | CAGGTGCAACTCAAGCAAAGCGGTGCAGAACTGGTGAGACCTGGCACATC AGTCAAGGTGTCATGCAAAGCTAGTGGATACGCCTTCACTAACTACCTGA TTGAGTGGGTGAAGCAAAGACCTGGTCAGGGTCTGGAATGGATTGGAGTG ATCAACCCAGGTAGCGGAGGAACTAACTACAACGAGAAGTTCAAGGATAA GGCAACTCTGACTGCCGACAAGAGCTCTAACACAGCCTATATGCAACTGT CCAGTCTCACTAGCGATGATTCCGCAGTGTACTTCTGTGCTCGCAGAGGC TGGGACTACTTTGACTACTGGGGTCAAGGAACTACTCTGACAGTGTCCAG C |
| 4 | 1B3_VL_nt | CAGATCGTTCTCACCCAGAGTCCTGCACTGATGTCAACAAGCCCTGGCGA GAAAGTTACAATGACTTGCAGTGCATCCTCTTCCGTTTCTTACATCTATT GGTTCCAGCAGAAGCCAGGGAGCTCACCAAAGCCTTGGATCTACAGAACA TCCAATCTCGCAAGCGGTGTTCCAGCTAGGTTCAGTGGGTCCGGATCAGG CACATCCTACTCTCTGACAATCTCCTCCATGGAAGCAGAAGACGCTGCAA CCTACTATTGCCAACAGTGGGACAACAATCCCTACACCTTTGGAGGTGGT ACCAAGCTGGAGATCAAG |
| 5 | 1B3_VH_CDR1_ aa | NYLIE |
| 6 | 1B3_VH_CDR2_ aa | VINPGSGGTNYNEKFKD |
| 7 | 1B3_VH_CDR3_ aa | RGWDYFDY |
| 8 | 1B3_VL_CDR1_ aa | SASSSVSYIY |
| 9 | 1B3_VL_CDR2_ aa | RTSNLAS |
| 10 | 1B3_VL_CDR3_ aa | QQWDNNPYT |
| 11 | SLAMF 6 (Q96DU3) | MLWLFQSLLFVFCFGPGNVVSQSSLIPLMVNGILGESVILPLEFPAGEKVNF ITWLFNETSLAFIVPHETKSPEIHVTNPKQGKRLNFTQSYSLQLSNLKMEDT GSYRAQISTKISAKLSSYTLRILRQLRNIQVINHSQLFQNMTCELHLTCSVE DADDNVSFRWEALGNTLSSQPNLTVSWDPRISSEQDYTCIAENAVSNLSFSV SAQKLCEDVKIQYTDTKMILFMVSGICIVFGFIILLLLVLRKRRDSLSLSTQ RTQGPAESARNLEYVSVSPINNTVYASVTHSNRETEIWTPRENDTITIYSTI NHSKESKPTFSRATALDNVV |
| 12 | SLAMF6 ECD (aa22-226 of SEQ ID NO: 11) | QSSLTPLMVNGILGESVILPLEFPAGEKVNFITWLFNETSLAFIVPHETKSP EIHVTNPKQGKRLNFTQSYSLQLSNLKMEDTGSYRAQISTKTSAKLSSYTLR ILRQLRNIQVINHSQLFQNMTCELHLTCSVEDADDNVSFRWEALGNTLSSQP NLTVSWDPRISSEQDYTCIAENAVSNLSFSVSAQKLCEDVKIQYTDTKM |
| 13 | 1B3_VHBhu aa | QVQLVQSGAE VKKPGASVKV SCKASGYAFT NYLIEWVRQA PGQGLEWIGV INPGSGGTNY NEKFQGRVTL TADKSISTAY MELSRLRSDD TAVYYCARRG WDYFDYWGQG TLVTVSS |
| 14 | 1B3VLBhu aa | DIQLTQSPSS LSASVGDRVT ITCQASQDVS YIYWYQQKPG KAPKPWIYRT SNLATGVPSR FSGSGSGTDY TFTISSLQPE DIATYYCQQW DNNPYTFGQG TKLEIK |
| 15 | 1B3_VHBhu_ CDR2 | VINPGSGGTNYNEKFQG |
| 16 | 1B3_VLBhu_ CDR1 | QASQDVSYIY |
| 17 | 1B3_VLBhu_ CDR2 | RTSNLAT |
| 18 | 1B3_VHBhu_ Fc_aa | QVQLVQSGAE VKKPGASVKV SCKASGYAFT NYLIEWVRQA PGQGLEWIGV INPGSGGTNY NEKFQGRVTL TADKSISTAY MELSRLRSDD TAVYYCARRG WDYFDYWGQG TLVTVSSAST |

-continued

Sequence List

| SEQ ID | Description | Sequence |
|---|---|---|
| | | KGPSVFPLAP SSKSTSGGTA ALGCLVKDYF PEPVTVSWNS<br>GALTSGVHTF PAVLQSSGLY SLSSVVTVPS SSLGTQTYIC<br>NVNHKPSNTK VDKKVEPKSC DKTHTCPPCP APEAAGGPSV<br>FLFPPKPKDT LMISRTPEVT CVVVDVSHED PEVKFNWYVD<br>GVEVHNAKTK PREEQYNSTY RVVSVLTVLH QDWLNGKEYK<br>CKVSNKALPA PIEKTISKAK GQPREPQVYT LPPSRDELTK<br>NQVSLTCLVK GFYPSDIAVE WESNGQPENN YKTTPPVLDS<br>DGSFFLYSKL TVDKSRWQQG NVFSCSVMHE ALHNHYTQKS<br>LSLSPGK |
| 19 | 1B3_VLBhu_<br>Fc_aa | DIQLTQSPSS LSASVGDRVT ITCQASQDVS YIYWYQQKPG<br>KAPKPWIYRT SNLATGVPSR FSGSGSGTDY TFTISSLQPE<br>DIATYYCQQW DNNPYTFGQG TKLEIKRTVA APSVFIFPPS<br>DEQLKSGTAS VVCLLNNFYP REAKVQWKVD NALQSGNSQE<br>SVTEQDSKDS TYSLSSTLTL SKADYEKHKV YACEVTHQGL<br>SSPVTKSFNR GEC |
| 20 | 1B3_VHBhu_nt | CAAGTGCAACTGGTGCAATCTGGTGCTGAAGTCAAGAAGCCTGGTGCTTCCG<br>TCAAGGTTTCTTGTAAGGCATCTGGTTACGCATTCACCAACTATCTCATTGA<br>ATGGGTTAGGCAAGCACCTGGACAAGGACTGGAGTGGATCGGAGTGATCAAC<br>CCAGGTTCTGGAGGCACAAACTACAACGAGAAGTTCCAAGGTCGCGTCACAC<br>TCACTGCAGACAAATCCATTTCTACAGCCTACATGGAGCTGTCTCGCCTCCG<br>CTCCGATGACACTGCTGTGTACTACTGCGCTCGCAGAGGTTGGGACTACTTC<br>GACTACTGGGGTCAAGGTACCCTCGTTACAGTGTCCAGC |
| 21 | 1B3_VLBhu_nt | GACATCCAACTGACTCAATCTCCATCTAGCCTGTCTGCATCCGTTGGTGATA<br>GGGTCACTATCACATGCCAAGCATCTCAAGACGTGAGCTACATCTATTGGTA<br>TCAACAGAAACCCGGTAAGGCTCCTAAACCTTGGATCTACAGGACATCTAAT<br>CTGGCCACTGGTGTTCCTTCTCGCTTCTCTGGCAGCGGTAGCGGAACCGACT<br>ACACTTTCACCATCAGCTCTCTCCAACCTGAAGACATTGCTACCTACTACTG<br>TCAGCAATGGGATAACAACCCATACACCTTTGGACAAGGTACCAAGCTGGAG<br>ATCAAG |
| 22 | 1B3_VHB_Fc_<br>nt | CAAGTGCAACTGGTGCAATCTGGTGCTGAAGTCAAGAAGCCTGGTGCTTCCG<br>TCAAGGTTTCTTGTAAGGCATCTGGTTACGCATTCACCAACTATCTCATTGA<br>ATGGGTTAGGCAAGCACCTGGACAAGGACTGGAGTGGATCGGAGTGATCAAC<br>CCAGGTTCTGGAGGCACAAACTACAACGAGAAGTTCCAAGGTCGCGTCACAC<br>TCACTGCAGACAAATCCATTTCTACAGCCTACATGGAGCTGTCTCGCCTCCG<br>CTCCGATGACACTGCTGTGTACTACTGCGCTCGCAGAGGTTGGGACTACTTC<br>GACTACTGGGGTCAAGGTACCCTCGTTACAGTGTCCAGCGCTAGCACCAAGG<br>GCCCATCCGTTTTCCCTCTGGCTCCTAGCTCCAAATCAACCAGCGGTGGCAC<br>AGCAGCCCTGGGATGTCTCGTGAAGGACTACTTCCCCGAGCCCGTCACCGTC<br>TCCTGGAACTCCGGCGCACTCACCTCCGGCGTCCACACCTTTCCCGCCGTTC<br>TGCAGAGTTCTGGCCTGTACAGTCTGAGTTCCGTGGTGACCGTCCCATCCTC<br>CTCCCTCGGGACCCAGACCTACATTTGTAATGTTAATCACAAGCCATCAAAC<br>ACCAAAGTGGATAAGAAGGTCGAACCTAAAAGCTGCGACAAGACTCACACCT<br>GCCCACCCTGCCCCGCACCAGAAGCTGCAGGTGGCCCCTCAGTTTTCCTGTT<br>CCCACCAAAGCCCAAAGATACCCTCATGATCTCAAGAACCCCAGAGGTCACC<br>TGCGTCGTCGTCGACGTGTCACACGAAGATCCCGAAGTCAAGTTTAATTGGT<br>ATGTTGATGGGGTCGAAGTGCATAACGCCAAAACAAAACCCCGCGAAGAGCA<br>GTATAACAGCACTTACAGAGTTGTTTCCGTTCTGACAGTGCTCCACCAGGAT<br>TGGCTGAATGGTAAGGAGTACAAATGCAAGGTGTCTAACAAGGCTCTGCCAG<br>CCCCTATTGAGAAAACCATAAGCAAGGCCAAGGGTCAGCCCAGGGAGCCACA<br>GGTGTATACCCTCCCACCTTCACGGGATGAGCTGACCAAGAACCAAGTGAGT<br>CTCACCTGTCTGGTGAAGGGCTTCTACCCAAGCGATATTGCTGTGGAATGGG<br>AATCTAACGGGCAGCCTGAAAATAACTACAAGACCACACCACCAGTGCTCGA<br>TTCCGACGGTAGCTTCTTTCTGTATTCCAAACTGACCGTGGACAAAAGCAGA<br>TGGCAGCAGGGAAATGTGTTCAGTTGTAGCGTGATGCATGAGGCCCTCCACA<br>ACCACTACACACAGAAGAGCCTCTCCCTGTCTCCCGGTAAG |
| 23 | 1B3_VLB_Fc_<br>nt | GACATCCAACTGACTCAATCTCCATCTAGCCTGTCTGCATCCGTTGGTGATA<br>GGGTCACTATCACATGCCAAGCATCTCAAGACGTGAGCTACATCTATTGGTA<br>TCAACAGAAACCCGGTAAGGCTCCTAAACCTTGGATCTACAGGACATCTAAT<br>CTGGCCACTGGTGTTCCTTCTCGCTTCTCTGGCAGCGGTAGCGGAACCGACT<br>ACACTTTCACCATCAGCTCTCTCCAACCTGAAGACATTGCTACCTACTACTG<br>TCAGCAATGGGATAACAACCCATACACCTTTGGACAAGGTACCAAGCTGGAG<br>ATCAAGAGAACAGTGGCTGCACCTAGTGTGTTCATCTTCCCTCCTTCCGATG<br>AGCAACTGAAGAGCGGAACCGCCAGTGTTGTCTGTCTGCTGAACAACTTCTA<br>CCCTCGGGAAGCCAAAGTTCAGTGGAAAGTCGACAACGCTCTGCAATCCGGC<br>AACTCCCAGGAGAGTGTCACAGAGCAAGATTCCAAGGACTCCACATATAGTC<br>TGTCCTCTACTCTGACTCTGAGCAAGGCTGACTACGAGAAGCACAAAGTGTA<br>CGCTTGCGAAGTGACACATCAAGGCCTGTCCAGTCCCGTTACCAAGAGCTTC<br>AATAGAGGAGAATGT |

The invention claimed is:

1. An isolated monoclonal antibody or an antigen-binding fragment thereof that binds to SLAMF6, said antibody or antigen binding fragment comprising:
   - (a) a heavy chain variable region comprising:
     - (i) a CDR-H1 sequence comprising SEQ ID NO: 5;
     - (ii) a CDR-H2 sequence comprising SEQ ID NO: 6 or SEQ ID NO:15; and
     - (iii) a CDR-H3 sequence comprising SEQ ID NO: 7; and
   - (b) a light chain variable region comprising:
     - (i) a CDR-L1 sequence comprising a sequence selected from the group consisting of SEQ ID NO: 8, and SEQ ID NO:16;
     - (ii) a CDR-L2 sequence comprising a sequence selected from the group consisting of SEQ ID NO: 9 and SEQ ID NO:17; and
     - (iii) a CDR-L3 sequence comprising SEQ ID NO: 10.

2. The antibody, or antigen-binding fragment, according to claim 1, wherein the heavy chain variable region comprises:
   - CDR-L1 comprising the sequence of SEQ ID NO: 5;
   - CDR-L2 comprising the sequence of SEQ ID NO: 15; and
   - CDR-L3 comprising the sequence of SEQ ID NO: 7.

3. The antibody, or antigen-binding fragment, according to claim 1, wherein the light chain variable region comprises:
   - CDR-L1 comprising the sequence of SEQ ID NO: 16;
   - CDR-L2 comprising the sequence of SEQ ID NO: 17; and
   - CDR-L3 comprising the sequence of SEQ ID NO: 10.

4. An isolated monoclonal antibody, or an antigen-binding fragment thereof, that binds to SLAMF6, said antibody or antigen binding fragment comprising:
   - a heavy chain variable region comprising:
     - a CDR-H1 comprising SEQ ID NO: 5;
     - a CDR-H2 comprising SEQ ID NO: 15; and
     - a CDR-H3 comprising SEQ ID NO: 7; and
   - a light chain variable region comprising:
     - a CDR-L1 comprising SEQ ID NO: 16;
     - a CDR-L2 comprising SEQ ID NO: 17; and
     - a CDR-L3 comprising SEQ ID NO: 10.

5. An antibody, or an antigen-binding fragment thereof, said antibody or antigen binding fragment comprising: i) the 3 heavy chain CDRs of SEQ ID NO:1 and the 3 light chain CDRs of SEQ ID NO: 2 or ii) the 3 heavy chain CDRs of SEQ ID NO:13 and the 3 light chain CDRs of SEQ ID NO:14, wherein the CDRs are each defined by the Kabat numbering system.

6. The antibody, or an antigen-binding fragment thereof, according to claim 1, comprising:
   - a heavy chain variable region comprising a sequence that is at least 80%, 85%, 90%, 91%, 92%, 93%, 94%, 95% 96% 97% 98% or 99% identical to SEQ ID NO: 13 and
   - a light chain variable region comprising a sequence that is at least 80%, 85%, 90%, 91%, 92%, 93%, 94%, 95% 96% 97% 98% or 99% identical to SEQ ID NO: 14.

7. The antibody, or an antigen-binding fragment thereof according to claim 6, comprising a heavy chain variable region comprising SEQ ID NO: 13, and a light chain variable region comprising SEQ ID NO: 14.

8. The antibody, or antigen-binding fragment thereof, according to claim 1, wherein the antibody or antigen binding fragment is a monoclonal antibody.

9. The antibody, or antigen-binding fragment thereof, according to claim 1, wherein the antibody or antigen binding fragment is chimeric, humanized, bispecific, or multispecific.

10. The antibody, or antigen-binding fragment thereof, according to claim 1, wherein the antibody or antigen-binding fragment is an Fc silenced engineered IgG1 antibody or antigen-binding fragment having reduced or no binding to one or more Fc receptors.

11. The antibody, or antigen-binding fragment thereof, according to claim 1, wherein the antibody or antigen-binding fragment is capable of inducing and/or enhancing T-cell cytotoxicity.

12. The antibody, or antigen-binding fragment thereof, according to claim 1, wherein the antigen-binding fragment is selected from the group consisting of: Fab, Fab', $F(ab)_2$, $F(ab')_2$, Fv, FV-TCR fragment, scFv, and single-domain antibody.

13. A pharmaceutical composition comprising the antibody, or antigen-binding fragment thereof, according to claim 1 and a pharmaceutically acceptable carrier.

14. A multispecific or bispecific antibody, or antigen-binding fragment thereof, comprising the monoclonal antibody of claim 1 and one or more additional antibody or antibody fragment thereof that binds to CD3 or PD-L1.

15. A polynucleotide encoding the heavy and light chain variable region of claim 7.

16. An expression vector comprising at least one polynucleotide according to claim 15.

17. A host cell comprising:

i. An expression vector comprising the polynucleotide according to claim 15; or ii. A first expression vector comprising a polynucleotide encoding the heavy chain variable region of an antibody or an antigen-binding portion thereof according to claim 15 and a second expression vector comprising a polynucleotide encoding the light chain variable region of the antibody or an antigen-binding portion thereof according to claim 15.

18. A method of making an antibody, or an antigen-binding fragment thereof, the method comprising culturing a host cell according to claim 17 under conditions wherein the antibody, or the antigen-binding fragment, is expressed in the host cell, and optionally isolating the antibody or antigen-binding fragment.

19. A method of treating a subject having cancer, the method comprising administering an effective amount of the antibody or antigen-binding fragment thereof of claim 1 to the subject.

20. The method according to claim 19, wherein said cancer is selected from the group consisting of small cell lung cancer, non-small cell lung cancer, squamous carcinomas, adenocarcinomas, skin cancer, melanoma, breast cancer, TNBC, colorectal cancer, gastric cancer, ovarian cancer, cervical cancer, prostate cancer, kidney cancer, liver cancer, hepatocellular carcinoma, pancreatic cancer, head and neck cancer, nasopharyngeal cancer, oesophageal cancer, bladder cancer and other uroepithelial cancers, stomach cancer, glioma, glioblastoma, testicular cancer, thyroid cancer, bone cancer, gallbladder and bile ducts cancers, uterine cancer, adrenal cancers, sarcomas, GIST, neuroendocrine tumours and haematological malignancies.

21. A method of treating a subject having cancer, the method comprising administering an effective amount of the pharmaceutical composition according to claim 13 to the subject.

22. The method according to claim 21, wherein the pharmaceutical composition further comprises an effective amount of a second therapeutic agent.

23. The method according to claim 21, wherein said cancer is selected from the group consisting of small cell lung cancer, non-small cell lung cancer, squamous carcinomas, and adenocarcinomas, skin cancer, melanoma, breast cancer, TNBC, colorectal cancer, gastric cancer, ovarian cancer, cervical cancer, prostate cancer, kidney cancer, liver cancer, hepatocellular carcinoma, pancreatic cancer, head and neck cancer, nasopharyngeal cancer, oesophageal cancer, bladder cancer and other uroepithelial cancers, stomach cancer, glioma, glioblastoma, testicular cancer, thyroid cancer, bone cancer, gallbladder and bile ducts cancers, uterine cancer, adrenal cancers, sarcomas, GIST, neuroendocrine tumours and haematological malignancies.

* * * * *

SEQUENCE LISTING

<160> NUMBER OF SEQ ID NOS: 23

<210> SEQ ID NO 1
<211> LENGTH: 117
<212> TYPE: PRT
<213> ORGANISM: mus musculus

<400> SEQUENCE: 1

```
Gln Val Gln Leu Lys Gln Ser Gly Ala Glu Leu Val Arg Pro Gly Thr
1               5                   10                  15

Ser Val Lys Val Ser Cys Lys Ala Ser Gly Tyr Ala Phe Thr Asn Tyr
            20                  25                  30

Leu Ile Glu Trp Val Lys Gln Arg Pro Gly Gln Gly Leu Glu Trp Ile
        35                  40                  45

Gly Val Ile Asn Pro Gly Ser Gly Gly Thr Asn Tyr Asn Glu Lys Phe
    50                  55                  60

Lys Asp Lys Ala Thr Leu Thr Ala Asp Lys Ser Ser Asn Thr Ala Tyr
65                  70                  75                  80

Met Gln Leu Ser Ser Leu Thr Ser Asp Asp Ser Ala Val Tyr Phe Cys
                85                  90                  95

Ala Arg Arg Gly Trp Asp Tyr Phe Asp Tyr Trp Gly Gln Gly Thr Thr
            100                 105                 110

Leu Thr Val Ser Ser
        115
```

<210> SEQ ID NO 2
<211> LENGTH: 106
<212> TYPE: PRT
<213> ORGANISM: mus musculus

<400> SEQUENCE: 2

```
Gln Ile Val Leu Thr Gln Ser Pro Ala Leu Met Ser Thr Ser Pro Gly
1               5                   10                  15

Glu Lys Val Thr Met Thr Cys Ser Ala Ser Ser Ser Val Ser Tyr Ile
            20                  25                  30

Tyr Trp Phe Gln Gln Lys Pro Gly Ser Ser Pro Lys Pro Trp Ile Tyr
        35                  40                  45

Arg Thr Ser Asn Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Asp Asn Asn Pro Tyr Thr
                85                  90                  95

Phe Gly Gly Gly Thr Lys Leu Glu Ile Lys
            100                 105
```

<210> SEQ ID NO 3
<211> LENGTH: 351
<212> TYPE: DNA
<213> ORGANISM: mus musculus

<400> SEQUENCE: 3

```
caggtgcaac tcaagcaaag cggtgcagaa ctggtgagac ctggcacatc agtcaaggtg      60

tcatgcaaag ctagtggata cgccttcact aactacctga ttgagtgggt gaagcaaaga     120

cctggtcagg gtctggaatg gattggagtg atcaacccag gtagcggagg aactaactac     180

aacgagaagt tcaaggataa ggcaactctg actgccgaca agagctctaa cacagcctat     240
```

atgcaactgt ccagtctcac tagcgatgat tccgcagtgt acttctgtgc tcgcagaggc 300
tgggactact ttgactactg gggtcaagga actactctga cagtgtccag c 351

<210> SEQ ID NO 4
<211> LENGTH: 318
<212> TYPE: DNA
<213> ORGANISM: mus musculus

<400> SEQUENCE: 4
cagatcgttc tcacccagag tcctgcactg atgtcaacaa gccctggcga gaaagttaca 60
atgacttgca gtgcatcctc ttccgtttct tacatctatt ggttccagca gaagccaggg 120
agctcaccaa agccttggat ctacagaaca tccaatctcg caagcggtgt tccagctagg 180
ttcagtgggt ccggatcagg cacatcctac tctctgacaa tctcctccat ggaagcagaa 240
gacgctgcaa cctactattg ccaacagtgg gacaacaatc cctacacctt tggaggtggt 300
accaagctgg agatcaag 318

<210> SEQ ID NO 5
<211> LENGTH: 5
<212> TYPE: PRT
<213> ORGANISM: mus musculus

<400> SEQUENCE: 5

Asn Tyr Leu Ile Glu
1 5

<210> SEQ ID NO 6
<211> LENGTH: 17
<212> TYPE: PRT
<213> ORGANISM: mus musculus

<400> SEQUENCE: 6

Val Ile Asn Pro Gly Ser Gly Gly Thr Asn Tyr Asn Glu Lys Phe Lys
1 5 10 15

Asp

<210> SEQ ID NO 7
<211> LENGTH: 8
<212> TYPE: PRT
<213> ORGANISM: mus musculus

<400> SEQUENCE: 7

Arg Gly Trp Asp Tyr Phe Asp Tyr
1 5

<210> SEQ ID NO 8
<211> LENGTH: 10
<212> TYPE: PRT
<213> ORGANISM: mus musculus

<400> SEQUENCE: 8

Ser Ala Ser Ser Ser Val Ser Tyr Ile Tyr
1 5 10

<210> SEQ ID NO 9
<211> LENGTH: 7
<212> TYPE: PRT
<213> ORGANISM: mus musculus

<400> SEQUENCE: 9

Arg Thr Ser Asn Leu Ala Ser

```
1               5


<210> SEQ ID NO 10
<211> LENGTH: 9
<212> TYPE: PRT
<213> ORGANISM: mus musculus

<400> SEQUENCE: 10

Gln Gln Trp Asp Asn Asn Pro Tyr Thr
1               5


<210> SEQ ID NO 11
<211> LENGTH: 332
<212> TYPE: PRT
<213> ORGANISM: Homo sapiens

<400> SEQUENCE: 11

Met Leu Trp Leu Phe Gln Ser Leu Leu Phe Val Phe Cys Phe Gly Pro
1               5                   10                  15

Gly Asn Val Val Ser Gln Ser Ser Leu Thr Pro Leu Met Val Asn Gly
            20                  25                  30

Ile Leu Gly Glu Ser Val Thr Leu Pro Leu Glu Phe Pro Ala Gly Glu
        35                  40                  45

Lys Val Asn Phe Ile Thr Trp Leu Phe Asn Glu Thr Ser Leu Ala Phe
    50                  55                  60

Ile Val Pro His Glu Thr Lys Ser Pro Glu Ile His Val Thr Asn Pro
65                  70                  75                  80

Lys Gln Gly Lys Arg Leu Asn Phe Thr Gln Ser Tyr Ser Leu Gln Leu
                85                  90                  95

Ser Asn Leu Lys Met Glu Asp Thr Gly Ser Tyr Arg Ala Gln Ile Ser
            100                 105                 110

Thr Lys Thr Ser Ala Lys Leu Ser Ser Tyr Thr Leu Arg Ile Leu Arg
        115                 120                 125

Gln Leu Arg Asn Ile Gln Val Thr Asn His Ser Gln Leu Phe Gln Asn
    130                 135                 140

Met Thr Cys Glu Leu His Leu Thr Cys Ser Val Glu Asp Ala Asp Asp
145                 150                 155                 160

Asn Val Ser Phe Arg Trp Glu Ala Leu Gly Asn Thr Leu Ser Ser Gln
                165                 170                 175

Pro Asn Leu Thr Val Ser Trp Asp Pro Arg Ile Ser Ser Glu Gln Asp
            180                 185                 190

Tyr Thr Cys Ile Ala Glu Asn Ala Val Ser Asn Leu Ser Phe Ser Val
        195                 200                 205

Ser Ala Gln Lys Leu Cys Glu Asp Val Lys Ile Gln Tyr Thr Asp Thr
    210                 215                 220

Lys Met Ile Leu Phe Met Val Ser Gly Ile Cys Ile Val Phe Gly Phe
225                 230                 235                 240

Ile Ile Leu Leu Leu Leu Val Leu Arg Lys Arg Arg Asp Ser Leu Ser
                245                 250                 255

Leu Ser Thr Gln Arg Thr Gln Gly Pro Ala Glu Ser Ala Arg Asn Leu
            260                 265                 270

Glu Tyr Val Ser Val Ser Pro Thr Asn Asn Thr Val Tyr Ala Ser Val
        275                 280                 285

Thr His Ser Asn Arg Glu Thr Glu Ile Trp Thr Pro Arg Glu Asn Asp
    290                 295                 300

Thr Ile Thr Ile Tyr Ser Thr Ile Asn His Ser Lys Glu Ser Lys Pro
```

305 310 315 320

Thr Phe Ser Arg Ala Thr Ala Leu Asp Asn Val Val
325 330

<210> SEQ ID NO 12
<211> LENGTH: 205
<212> TYPE: PRT
<213> ORGANISM: Homo sapiens

<400> SEQUENCE: 12

Gln Ser Ser Leu Thr Pro Leu Met Val Asn Gly Ile Leu Gly Glu Ser
1 5 10 15

Val Thr Leu Pro Leu Glu Phe Pro Ala Gly Glu Lys Val Asn Phe Ile
20 25 30

Thr Trp Leu Phe Asn Glu Thr Ser Leu Ala Phe Ile Val Pro His Glu
35 40 45

Thr Lys Ser Pro Glu Ile His Val Thr Asn Pro Lys Gln Gly Lys Arg
50 55 60

Leu Asn Phe Thr Gln Ser Tyr Ser Leu Gln Leu Ser Asn Leu Lys Met
65 70 75 80

Glu Asp Thr Gly Ser Tyr Arg Ala Gln Ile Ser Thr Lys Thr Ser Ala
85 90 95

Lys Leu Ser Ser Tyr Thr Leu Arg Ile Leu Arg Gln Leu Arg Asn Ile
100 105 110

Gln Val Thr Asn His Ser Gln Leu Phe Gln Asn Met Thr Cys Glu Leu
115 120 125

His Leu Thr Cys Ser Val Glu Asp Ala Asp Asp Asn Val Ser Phe Arg
130 135 140

Trp Glu Ala Leu Gly Asn Thr Leu Ser Ser Gln Pro Asn Leu Thr Val
145 150 155 160

Ser Trp Asp Pro Arg Ile Ser Ser Glu Gln Asp Tyr Thr Cys Ile Ala
165 170 175

Glu Asn Ala Val Ser Asn Leu Ser Phe Ser Val Ser Ala Gln Lys Leu
180 185 190

Cys Glu Asp Val Lys Ile Gln Tyr Thr Asp Thr Lys Met
195 200 205

<210> SEQ ID NO 13
<211> LENGTH: 117
<212> TYPE: PRT
<213> ORGANISM: Artificial Sequence
<220> FEATURE:
<223> OTHER INFORMATION: Humanised antibody sequence

<400> SEQUENCE: 13

Gln Val Gln Leu Val Gln Ser Gly Ala Glu Val Lys Lys Pro Gly Ala
1 5 10 15

Ser Val Lys Val Ser Cys Lys Ala Ser Gly Tyr Ala Phe Thr Asn Tyr
20 25 30

Leu Ile Glu Trp Val Arg Gln Ala Pro Gly Gln Gly Leu Glu Trp Ile
35 40 45

Gly Val Ile Asn Pro Gly Ser Gly Gly Thr Asn Tyr Asn Glu Lys Phe
50 55 60

Gln Gly Arg Val Thr Leu Thr Ala Asp Lys Ser Ile Ser Thr Ala Tyr
65 70 75 80

Met Glu Leu Ser Arg Leu Arg Ser Asp Asp Thr Ala Val Tyr Tyr Cys
85 90 95

```
Ala Arg Arg Gly Trp Asp Tyr Phe Asp Tyr Trp Gly Gln Gly Thr Leu
            100                 105                 110

Val Thr Val Ser Ser
        115


<210> SEQ ID NO 14
<211> LENGTH: 106
<212> TYPE: PRT
<213> ORGANISM: Artificial Sequence
<220> FEATURE:
<223> OTHER INFORMATION: Humanised antibody sequence

<400> SEQUENCE: 14

Asp Ile Gln Leu Thr Gln Ser Pro Ser Ser Leu Ser Ala Ser Val Gly
1               5                   10                  15

Asp Arg Val Thr Ile Thr Cys Gln Ala Ser Gln Asp Val Ser Tyr Ile
            20                  25                  30

Tyr Trp Tyr Gln Gln Lys Pro Gly Lys Ala Pro Lys Pro Trp Ile Tyr
        35                  40                  45

Arg Thr Ser Asn Leu Ala Thr Gly Val Pro Ser Arg Phe Ser Gly Ser
    50                  55                  60

Gly Ser Gly Thr Asp Tyr Thr Phe Thr Ile Ser Ser Leu Gln Pro Glu
65                  70                  75                  80

Asp Ile Ala Thr Tyr Tyr Cys Gln Gln Trp Asp Asn Asn Pro Tyr Thr
                85                  90                  95

Phe Gly Gln Gly Thr Lys Leu Glu Ile Lys
            100                 105


<210> SEQ ID NO 15
<211> LENGTH: 17
<212> TYPE: PRT
<213> ORGANISM: Artificial Sequence
<220> FEATURE:
<223> OTHER INFORMATION: Humanised CDR sequence

<400> SEQUENCE: 15

Val Ile Asn Pro Gly Ser Gly Gly Thr Asn Tyr Asn Glu Lys Phe Gln
1               5                   10                  15

Gly


<210> SEQ ID NO 16
<211> LENGTH: 10
<212> TYPE: PRT
<213> ORGANISM: Artificial Sequence
<220> FEATURE:
<223> OTHER INFORMATION: Humanised CDR sequence

<400> SEQUENCE: 16

Gln Ala Ser Gln Asp Val Ser Tyr Ile Tyr
1               5                   10


<210> SEQ ID NO 17
<211> LENGTH: 7
<212> TYPE: PRT
<213> ORGANISM: Artificial Sequence
<220> FEATURE:
<223> OTHER INFORMATION: Humanised CDR sequence

<400> SEQUENCE: 17

Arg Thr Ser Asn Leu Ala Thr
1               5
```

<210> SEQ ID NO 18
<211> LENGTH: 447
<212> TYPE: PRT
<213> ORGANISM: Artificial Sequence
<220> FEATURE:
<223> OTHER INFORMATION: Humanised antibody sequence

<400> SEQUENCE: 18

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asn Tyr
            20                  25                  30

Leu Ile Glu Trp Val Arg Gln Ala Pro Gly Gln Gly Leu Glu Trp Ile
        35                  40                  45

Gly Val Ile Asn Pro Gly Ser Gly Gly Thr Asn Tyr Asn Glu Lys Phe
    50                  55                  60

Gln Gly Arg Val Thr Leu Thr Ala Asp Lys Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Arg Gly Trp Asp Tyr Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365
```

```
Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445


<210> SEQ ID NO 19
<211> LENGTH: 213
<212> TYPE: PRT
<213> ORGANISM: Artificial Sequence
<220> FEATURE:
<223> OTHER INFORMATION: Humanised antibody sequence

<400> SEQUENCE: 19

Asp Ile Gln Leu Thr Gln Ser Pro Ser Ser Leu Ser Ala Ser Val Gly
1               5                   10                  15

Asp Arg Val Thr Ile Thr Cys Gln Ala Ser Gln Asp Val Ser Tyr Ile
            20                  25                  30

Tyr Trp Tyr Gln Gln Lys Pro Gly Lys Ala Pro Lys Pro Trp Ile Tyr
        35                  40                  45

Arg Thr Ser Asn Leu Ala Thr Gly Val Pro Ser Arg Phe Ser Gly Ser
    50                  55                  60

Gly Ser Gly Thr Asp Tyr Thr Phe Thr Ile Ser Ser Leu Gln Pro Glu
65                  70                  75                  80

Asp Ile Ala Thr Tyr Tyr Cys Gln Gln Trp Asp Asn Asn Pro Tyr Thr
                85                  90                  95

Phe Gly Gln Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210


<210> SEQ ID NO 20
<211> LENGTH: 351
<212> TYPE: DNA
<213> ORGANISM: Artificial Sequence
<220> FEATURE:
<223> OTHER INFORMATION: Humanised antibody sequence

<400> SEQUENCE: 20

caagtgcaac tggtgcaatc tggtgctgaa gtcaagaagc ctggtgcttc cgtcaaggtt     60
```

```
tcttgtaagg catctggtta cgcattcacc aactatctca ttgaatgggt taggcaagca    120

cctggacaag gactggagtg gatcggagtg atcaacccag gttctggagg cacaaactac    180

aacgagaagt tccaaggtcg cgtcacactc actgcagaca aatccatttc tacagcctac    240

atggagctgt ctcgcctccg ctccgatgac actgctgtgt actactgcgc tcgcagaggt    300

tgggactact tcgactactg ggtcaaggt accctcgtta cagtgtccag c              351


<210> SEQ ID NO 21
<211> LENGTH: 318
<212> TYPE: DNA
<213> ORGANISM: Artificial Sequence
<220> FEATURE:
<223> OTHER INFORMATION: Humanised antibody sequence

<400> SEQUENCE: 21

gacatccaac tgactcaatc tccatctagc ctgtctgcat ccgttggtga tagggtcact     60

atcacatgcc aagcatctca agacgtgagc tacatctatt ggtatcaaca gaaacccggt    120

aaggctccta aaccttggat ctacaggaca tctaatctgg ccactggtgt tccttctcgc    180

ttctctggca gcggtagcgg aaccgactac actttcacca tcagctctct ccaacctgaa    240

gacattgcta cctactactg tcagcaatgg gataacaacc catacacctt tggacaaggt    300

accaagctgg agatcaag                                                  318


<210> SEQ ID NO 22
<211> LENGTH: 1341
<212> TYPE: DNA
<213> ORGANISM: Artificial Sequence
<220> FEATURE:
<223> OTHER INFORMATION: Humanised antibody sequence

<400> SEQUENCE: 22

caagtgcaac tggtgcaatc tggtgctgaa gtcaagaagc ctggtgcttc cgtcaaggtt     60

tcttgtaagg catctggtta cgcattcacc aactatctca ttgaatgggt taggcaagca    120

cctggacaag gactggagtg gatcggagtg atcaacccag gttctggagg cacaaactac    180

aacgagaagt tccaaggtcg cgtcacactc actgcagaca aatccatttc tacagcctac    240

atggagctgt ctcgcctccg ctccgatgac actgctgtgt actactgcgc tcgcagaggt    300

tgggactact tcgactactg ggtcaaggt accctcgtta cagtgtccag cgctagcacc    360

aagggcccat ccgttttccc tctggctcct agctccaaat caaccagcgg tggcacagca    420

gccctgggat gtctcgtgaa ggactacttc cccgagcccg tcaccgtctc ctggaactcc    480

ggcgcactca cctccggcgt ccacaccttt cccgccgttc tgcagagttc tggcctgtac    540

agtctgagtt ccgtggtgac cgtcccatcc tcctccctcg ggacccagac ctacatttgt    600

aatgttaatc acaagccatc aaacaccaaa gtggataaga aggtcgaacc taaaagctgc    660

gacaagactc acacctgccc accctgcccc gcaccagaag ctgcaggtgg cccctcagtt    720

ttcctgttcc caccaaagcc caaagatacc ctcatgatct caagaacccc agaggtcacc    780

tgcgtcgtcg tcgacgtgtc acacgaagat cccgaagtca agtttaattg gtatgttgat    840

ggggtcgaag tgcataacgc caaaacaaaa ccccgcgaag agcagtataa cagcacttac    900

agagttgttt ccgttctgac agtgctccac caggattggc tgaatggtaa ggagtacaaa    960

tgcaaggtgt ctaacaaggc tctgccagcc cctattgaga aaaccataag caaggccaag   1020

ggtcagccca gggagccaca ggtgtatacc ctcccacctt cacgggatga gctgaccaag   1080

aaccaagtga gtctcacctg tctggtgaag ggcttctacc caagcgatat tgctgtggaa   1140
```

-continued

```
tgggaatcta acgggcagcc tgaaaataac tacaagacca caccaccagt gctcgattcc   1200

gacggtagct tctttctgta ttccaaactg accgtggaca aaagcagatg gcagcaggga   1260

aatgtgttca gttgtagcgt gatgcatgag gccctccaca accactacac acagaagagc   1320

ctctccctgt ctcccggtaa g                                              1341


<210> SEQ ID NO 23
<211> LENGTH: 639
<212> TYPE: DNA
<213> ORGANISM: Artificial Sequence
<220> FEATURE:
<223> OTHER INFORMATION: Humanised antibody sequence

<400> SEQUENCE: 23

gacatccaac tgactcaatc tccatctagc ctgtctgcat ccgttggtga tagggtcact     60

atcacatgcc aagcatctca agacgtgagc tacatctatt ggtatcaaca gaaacccggt    120

aaggctccta aaccttggat ctacaggaca tctaatctgg ccactggtgt tccttctcgc    180

ttctctggca gcggtagcgg aaccgactac actttcacca tcagctctct ccaacctgaa    240

gacattgcta cctactactg tcagcaatgg gataacaacc catacacctt tggacaaggt    300

accaagctgg agatcaagag aacagtggct gcacctagtg tgttcatctt ccctccttcc    360

gatgagcaac tgaagagcgg aaccgccagt gttgtctgtc tgctgaacaa cttctaccct    420

cgggaagcca aagttcagtg gaaagtcgac aacgctctgc aatccggcaa ctcccaggag    480

agtgtcacag agcaagattc caaggactcc acatatagtc tgtcctctac tctgactctg    540

agcaaggctg actacgagaa gcacaaagtg tacgcttgcg aagtgacaca tcaaggcctg    600

tccagtcccg ttaccaagag cttcaataga ggagaatgt                           639
```